(12) United States Patent
Vuillemin et al.

(10) Patent No.: US 10,316,300 B2
(45) Date of Patent: Jun. 11, 2019

(54) PROTEIN WITH DEXTRAN-SACCHARASE ACTIVITY, AND USES

(71) Applicants: INSTITUT NATIONAL DES SCIENCES APPLIQUÉES DE TOULOUSE, Toulouse (FR); INSTITUT NATIONAL DE LA RECHERCHE AGRONOMIQUE, Paris (FR); CENTRE NATIONAL DE LA RECHERCHE SCIENTIFIQUE, Paris (FR); UNIVERSITE PAUL SABATIER TOULOUSE III, Toulouse (FR)

(72) Inventors: Marlène Vuillemin, Ramonville-Saint-Agne (FR); Marion Claverie, Benejacq (FR); Claire Moulis, Viellevigne (FR); Magali Remaud-Simeon, Ramonville-Saint-Agne (FR); Pierre Monsan, Mondonville (FR); Etienne Severac, Pibrac (FR); Catherine Fontagne-Faucher, L'Isle Jourdain (FR)

(73) Assignees: INSTITUT NATIONAL DES SCIENCES APPLIQUEES TOULOUSE, Toulouse (FR); INSTITUT NATIONAL DE LA RECHERCHE AGRONOMIQUE, Paris (FR); CENTRE NATIONAL DE LA RECHERCHE SCIENTIFIQUE, Paris (FR); UNIVERSITE PAUL SABATIER TOULOUSE III, Toulouse (FR)

( * ) Notice: Subject to any disclaimer, the term of this patent is extended or adjusted under 35 U.S.C. 154(b) by 74 days.

(21) Appl. No.: 15/329,941

(22) PCT Filed: Jul. 21, 2015

(86) PCT No.: PCT/FR2015/052002
§ 371 (c)(1),
(2) Date: Jan. 27, 2017

(87) PCT Pub. No.: WO2016/016544
PCT Pub. Date: Feb. 4, 2016

(65) Prior Publication Data
US 2017/0247669 A1 Aug. 31, 2017

(30) Foreign Application Priority Data
Jul. 28, 2014 (FR) ..................................... 14 57264

(51) Int. Cl.
*A61K 8/73* (2006.01)
*C12N 9/10* (2006.01)
*A61K 47/36* (2006.01)
*C08B 37/02* (2006.01)
*C12P 19/08* (2006.01)
*C12P 19/18* (2006.01)
*A23L 29/269* (2016.01)
*A61K 31/721* (2006.01)

(52) U.S. Cl.
CPC .......... *C12N 9/1051* (2013.01); *A23L 29/273* (2016.08); *A61K 8/73* (2013.01); *A61K 31/721* (2013.01); *A61K 47/36* (2013.01); *C08B 37/0021* (2013.01); *C12P 19/08* (2013.01); *C12P 19/18* (2013.01); *C12Y 204/01005* (2013.01); *A23V 2002/00* (2013.01)

(58) Field of Classification Search
CPC ........... C12P 19/18; C12P 19/04; C12P 19/08; C12N 9/1048
See application file for complete search history.

(56) References Cited

U.S. PATENT DOCUMENTS

| 4,649,058 A | 3/1987 | Schwengers |
| 4,767,614 A | 8/1988 | Scarpa et al. |
| 5,229,277 A | 7/1993 | Day et al. |

FOREIGN PATENT DOCUMENTS

| EP | 0164656 A2 | 12/1985 |
| WO | 2010/128859 A2 | 11/2010 |
| WO | 2010/129839 A1 | 11/2010 |

OTHER PUBLICATIONS

Anonymous, "Dextrans," URL: http://web.archive.org/web/20140120040848/http://www.sigmaaldrich.com/life-science/biochemicals/biochemical-products.html, retrieved Oct. 5, 2015, 4 pages.
Caligur, "Dextrans and Related Polysaccharides," BioFiles 2008, 7 pages.
Dols et al., "Characterization of the Different Dextransucrase Activities Excreted in Glucose, Fructose, or Sucrose Medium by *Leuconostoc mesenteroides* NRRL B-1299," *Applied and Environmental Microbiology* 64(4):1298-1302, 1998.

(Continued)

*Primary Examiner* — Kagnew H Gebreyesus
(74) *Attorney, Agent, or Firm* — Seed Intellectual Property Law Group LLP

(57) ABSTRACT

The invention relates to: —a protein having dextran-saccharase activity and the sequence SEQ ID NO: 1 for an amino acid sequence; —a protein having dextran-saccharase activity and the sequence SEQ ID NO: 2 for an amino acid sequence; —a complex containing a substrate and a protein with dextran-saccharase activity —a method for synthesizing dextrans; and —dextrans. The invention also relates to a method for synthesizing gluco-oligosaccharides and gluco-conjugates and to the resulting products.

Figure 1:
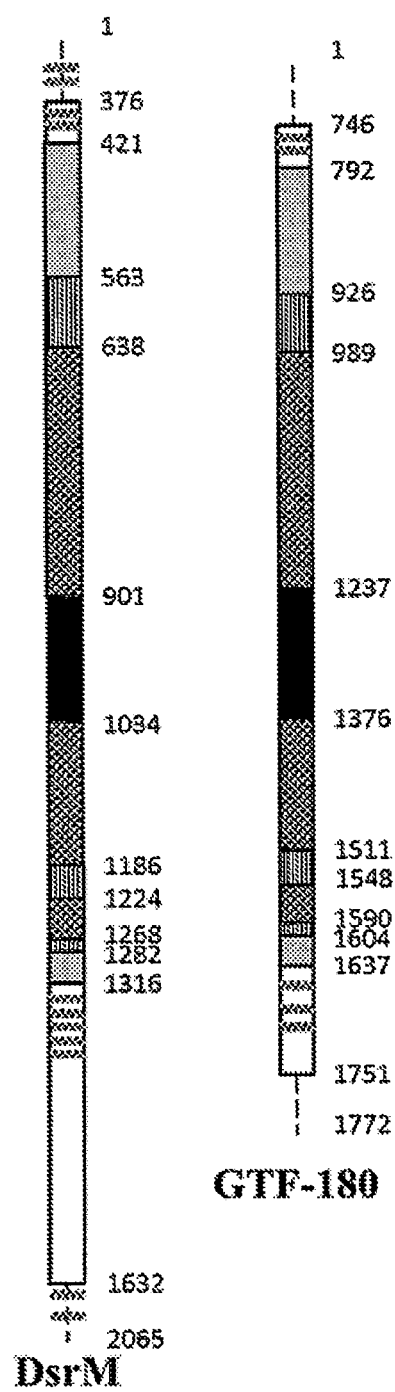

21 Claims, 22 Drawing Sheets
Specification includes a Sequence Listing.

(56) References Cited

OTHER PUBLICATIONS

Khalikova et al., "Microbial Dextran-Hydrolyzing Enzymes: Fundamentals and Applications," *Microbiology and Molecular Biology Reviews* 69(2):306-325, 2005.
Simpson et al., "Four glucosyltransferases, GtfJ, GtfK, GtfL and GtfM, from *Streptococcus salivarius* ATCC 25975," *Microbiology* 141:1451-1460, 1995.
Van Hijum et al., "Structure-Function Relationships of Glucansucrase and Fructansucrase Enzymes from Lactic Acid Bacteria," *Microbiology and Molecular Biology Reviews* 70(1):157-176, 2006.
Database Accession No. UNIPROT:A0A0A1IPZ8, Feb. 4, 2015, 2 pages.

| Support | Supplier | Nature of support | Functional group | Type of bond |
|---|---|---|---|---|
| Sepabeads AA130 | Spin Technologies | highly porous Polymethacrylate | Amino group (short spacer) | Ionic bonds |
| Sepabeads AO110 | Spin Technologies | Polymethacrylate Polystyrene – DiVinyl-Benzene | Octadecyl group | Hydrophobic bonds |
| Sepabeads SM110 | Spin Technologies |  | – – | Hydrophobic bonds |
| Sepabeads ECQ1A | Resindion | Polymethacrylate | Quaternary amine group -NR³⁺ | Ionic bonds |
| Purolite ECR1604 | Purolite | Styrene | Quaternary amine group -NR³⁺ | Ionic bonds |
| Purolite ECR8214 | Purolite | Epoxy methacrylate | Epoxy group | Covalent bonds |
| Purolite ECR4204 | Purolite | Epoxy methacrylic/Styrene | Epoxy group | Covalent bonds |

Figure 3

SEQUENCE LISTING

```
<160> NUMBER OF SEQ ID NOS: 6

<210> SEQ ID NO 1
<211> LENGTH: 2065
<212> TYPE: PRT
<213> ORGANISM: Artificial Sequence
<220> FEATURE:
<223> OTHER INFORMATION: Dextrane saccharase

<400> SEQUENCE: 1

Met Lys Ile Lys Glu Thr Ile Thr Arg Lys Lys Leu Tyr Lys Ser Gly
1               5                   10                  15

Lys Ser Trp Val Ala Ala Ala Thr Ala Phe Ala Val Met Gly Val Ser
            20                  25                  30

Ala Val Thr Thr Val Ser Ala Asp Thr Gln Thr Pro Val Gly Thr Thr
        35                  40                  45

Gln Ser Gln Gln Asp Leu Thr Gly Gln Thr Gly Gln Asp Lys Pro Thr
    50                  55                  60

Thr Lys Glu Val Ile Asp Lys Lys Glu Pro Val Pro Arg Val Ser Ala
65                  70                  75                  80

Gln Asn Ala Gly Asp Leu Ser Ala Asp Ala Lys Thr Thr Lys Ala Asp
                85                  90                  95

Asp Lys Gln Asp Thr Gln Pro Thr Asn Ala Gln Leu Pro Asp Gln Gly
            100                 105                 110

Asn Lys Gln Thr Asn Ser Asn Ser Asp Lys Gly Val Lys Glu Ser Thr
        115                 120                 125

Thr Ala Pro Val Lys Thr Thr Asp Val Pro Ser Lys Ser Val Ala Pro
    130                 135                 140

Glu Thr Asn Thr Ser Ile Asn Ala Ser Asp Ala Ile Ser Lys Ser Gln
145                 150                 155                 160

Glu Lys Gln Phe Glu Lys Ala Pro Asp Ser Val Pro Glu Thr Ile Thr
                165                 170                 175
```

-continued

```
Gly Gly Arg Tyr Ser Leu Lys Asp Gly Tyr Val Tyr Leu Asp Lys
            180                 185                 190

Gln Gly Lys Gln Val Val Gly Pro Lys Asn Ile Asp Asn His Leu Gln
        195                 200                 205

Tyr Phe Asp Glu Thr Thr Gly Lys Gln Val Lys Gly Asp Phe Arg Ser
    210                 215                 220

Val Asn Gly Lys Arg Ile Tyr Phe Asn Ala Asn Leu Gly Tyr Ala Asp
225                 230                 235                 240

Asp Tyr Thr Thr Asp Val Ala Gly Lys Leu Val Gly Tyr Asp Ser Asn
                245                 250                 255

Gly Asn Gln Val Lys Ala Gly Tyr Val Thr Asn Ser Gln Gly Lys Thr
            260                 265                 270

Tyr Tyr Phe Asn Asn Gln Gly Glu Ala Ile Ile Gly Leu Lys Thr Asp
        275                 280                 285

Asn Asn Lys Thr Gln Tyr Phe Gly Pro Asp Gly Ala Gln Val Lys Gly
    290                 295                 300

Ala Phe Gln Gln Val Asn Gly Lys Asn Ile Tyr Phe Asp Ala Gln Thr
305                 310                 315                 320

Gly Tyr Ala Arg Gln Asn Val Gly Phe Leu Asp Gly Thr Ala Lys Gly
                325                 330                 335

Phe Asp Glu Gln Gly Asn Gln Ile Lys Ser Gly Ile Ala Thr Asp Leu
            340                 345                 350

Ser Gly Asn Val Tyr Tyr Phe Asp Ala Ser Gly Lys Met Leu Thr Gly
        355                 360                 365

Val Gln Asn Ile Asp Gly Lys Lys Tyr Tyr Phe Asp Glu Gln Gly His
    370                 375                 380

Arg Arg Arg Asn Tyr Ala Gly Val Phe Asn Asn Glu Phe Ile Tyr Phe
385                 390                 395                 400

Gly Leu Asp Gly Val Gly Gln Ser Ala Ile Glu Tyr Gln Phe Glu Lys
                405                 410                 415

Gly Leu Thr Ser Gln Asn Ser Val Ala Thr Ser His Asn Ala Ala Lys
            420                 425                 430

Ser Tyr Asp Thr Lys Ser Phe Thr Asn Val Asp Gly Phe Leu Thr Ala
        435                 440                 445

Asn Ser Trp Tyr Arg Pro Thr Asp Ile Leu Arg Asn Gly Thr Lys Trp
    450                 455                 460

Glu Pro Ser Thr Glu Thr Asp Phe Arg Pro Leu Leu Met Thr Trp Trp
465                 470                 475                 480

Pro Asp Lys Glu Val Gln Ala Asn Tyr Leu Asn Tyr Met Ser Ala Leu
                485                 490                 495

Gly Leu Gly Asp Gln Lys Ile Tyr Thr Gly Ala Ser Ser Gln Leu Asp
            500                 505                 510

Leu Asn Asn Ala Ala Leu Ile Val Gln Glu Ala Ile Glu Lys Lys Ile
        515                 520                 525

Ser Leu Glu Lys Ser Thr Lys Trp Leu Asp Asp Ser Ile Lys Ser Phe
    530                 535                 540

Ile Lys Ser Lys Arg Lys Asp Ile Gln Gly Asn Leu Val Asp Thr Asn
545                 550                 555                 560

Pro Gly Trp Thr Ile Asp Ser Glu Thr Gly Ser Thr Asn His Leu Gln
                565                 570                 575

Asn Gly Ala Phe Ile Phe Thr Asn Ser Pro Leu Val Pro Glu Ala Asn
            580                 585                 590
```

```
-continued

Ala Ala Glu Gly Asn Arg Leu Ile Asn Arg Thr Pro Ser Gln Gln Thr
        595                 600                 605

Gly Asn His Ile Ser Tyr Ala Ser Gln Pro Tyr Ser Gly Asp Asp Trp
        610                 615                 620

Gly Tyr Glu Leu Leu Leu Gly Asn Asp Val Asp Asn Ser Asn Pro Ile
625                 630                 635                 640

Val Gln Ala Glu Gln Leu Asn Trp Ile His Tyr Leu Met Asn Phe Gly
                645                 650                 655

Thr Ile Thr Ala Pro Gln Asp Pro Asp Ala His Leu Ala Asn Phe Asp
                660                 665                 670

Ser Ile Arg Ile Asp Ala Val Asp Asn Val Asp Ala Asp Leu Leu Gln
            675                 680                 685

Ile Ala Gly Asp Tyr Phe Lys Ala Ala Tyr Gln Val Gly Glu Asn Asp
        690                 695                 700

Lys Asn Ala Asn Gln His Ile His Ile Leu Glu Asp Trp Ser Pro Asn
705                 710                 715                 720

Asp Val Trp Tyr Asn Gln Gln Val Asn Gly Asn Ser Gln Leu Thr Met
                725                 730                 735

Asp Ala Thr Met Gln Asn Gln Leu Leu Ala Ser Leu Thr Arg Pro Ile
                740                 745                 750

Thr Ser Arg Asp Ser Met Lys Ser Phe Thr Lys Asp Ala Leu Leu Val
    755                 760                 765

His Arg Thr Ala Asp Asn Ser Tyr Asn Gln Ala Val Pro Asn Tyr Ser
    770                 775                 780

Phe Ile Arg Ala His Asp Ser Glu Val Gln Thr Ile Ala Lys Ile
785                 790                 795                 800

Ile Ser Asp Lys His Pro Asp Leu Tyr Pro Thr Val Asp Lys Ala Leu
                805                 810                 815

Leu Ala Lys Asp Ser Ala Leu Tyr Asp Glu Ala Phe Thr Glu Tyr Asn
                820                 825                 830

Ala Asp Met Gln Lys Ile Ser Ser Gln Lys Tyr Thr His Asn Asn
                835                 840                 845

Met Pro Ser Ala Tyr Ala Ile Leu Leu Thr Asn Lys Asp Thr Val Pro
850                 855                 860

Arg Val Tyr Tyr Gly Asp Leu Phe Thr Asp Asn Gly Glu Tyr Met Ala
865                 870                 875                 880

Asn Lys Thr Pro Tyr Tyr Asp Ala Ile Thr Ser Leu Leu Thr Ala Arg
                885                 890                 895

Thr Lys Phe Val Ser Gly Gly Gln Ser Leu Ser Val Asp Lys Asn Asp
                900                 905                 910

Val Leu Thr Ser Val Arg Tyr Gly Lys Gly Ala Leu Ser Ala Thr Asp
            915                 920                 925

Asn Gly Ser Ser Asp Thr Arg Asn Gln Gly Ile Gly Val Ile Val Ser
    930                 935                 940

Asn Asn Pro Asn Leu Asp Leu Asn Asn Asp Lys Val Thr Leu Ser Met
945                 950                 955                 960

Gly Ile Ser His Ala His Gln Ala Tyr Arg Pro Leu Leu Thr Asn
                965                 970                 975

Ser Gln Gly Ile Val Ala Tyr Ala Thr Asp Ser Glu Val Pro Gln Asn
            980                 985                 990

Leu Tyr Lys Thr Thr Asn Asp Lys  Gly Glu Leu Thr Phe Asp Ala Ser
        995                 1000                 1005

Glu Ile  Lys Gly Tyr Asp Thr  Val Gln Thr Ser Gly  Tyr Leu Ala
```

-continued

```
            1010                1015                1020
Val Trp Val Pro Val Gly Ala Ser Asp Glu Gln Asp Ala Arg Thr
    1025            1030                1035
Ile Ala Ser Thr Glu Lys Asn Asn Gly Asn Ser Val Tyr His Ser
    1040            1045                1050
Asn Ala Ala Leu Asp Ser Gln Leu Ile Tyr Glu Gly Phe Ser Asn
    1055            1060                1065
Phe Gln Thr Val Pro Ser Lys Asn Ala Ser Ala Asp Glu Tyr Ala
    1070            1075                1080
Asn Val Ile Ile Ala Lys His Ala Ala Asp Phe Asn Lys Trp Gly
    1085            1090                1095
Val Thr Ser Phe Gln Met Ala Pro Gln Tyr Arg Ser Ser Thr Asp
    1100            1105                1110
Gly Ser Phe Leu Asp Ala Val Asp Thr Val Gln Asn Gly Tyr Ala
    1115            1120                1125
Phe Thr Asp Arg Tyr Asp Leu Gly Phe Asn Ala Ala Asp Gly Ser
    1130            1135                1140
Lys Asn Pro Thr Lys Tyr Gly Thr Asp Glu Asp Leu Arg Asn Ala
    1145            1150                1155
Ile Lys Ser Leu His Ala Gln Lys Thr Tyr Asp Gly Ser Ser Ile
    1160            1165                1170
Gln Val Met Ala Asp Phe Val Pro Asp Gln Leu Tyr Asn Met Pro
    1175            1180                1185
Leu Glu Gln Ala Val Ser Val Ile Arg Thr Asp Lys Tyr Gly Val
    1190            1195                1200
Asn Ser Glu Asn Pro Asp Ile Gln Asn Ile Ile Tyr Ala Ala Asn
    1205            1210                1215
Ile Lys Ser Ser Gly Thr Asp Tyr Gln Ser Ile Tyr Gly Gly Lys
    1220            1225                1230
Tyr Leu Ala Glu Leu Gln Lys Asn Pro Leu Phe Lys Ser Leu Phe
    1235            1240                1245
Asp Arg Ile Gln Ile Ser Thr Lys Lys Thr Ile Asp Pro Asn Thr
    1250            1255                1260
Arg Ile Thr Gln Trp Ser Ala Lys Tyr Phe Asn Gly Ser Asn Ile
    1265            1270                1275
Gln Gly Lys Gly Ile Asn Tyr Val Leu Lys Asp Trp Ala Ser Asn
    1280            1285                1290
Lys Tyr Phe Asn Val Ser Ser Asn Asp Asp Met Tyr Ser Arg Leu
    1295            1300                1305
Pro Lys Gln Leu Met Asn Gln Glu Ser Asn Thr Gly Phe Ile Val
    1310            1315                1320
Asp Asp Ile Gly Val Lys Tyr Tyr Ser Ile Ser Gly Tyr Gln Ala
    1325            1330                1335
Lys Asn Thr Phe Val Glu Asp Gly Asn Gly Glu Trp Tyr Tyr Phe
    1340            1345                1350
Asp Asn Asp Gly Tyr Met Val Lys Ser Thr Glu Glu Ser Gly Pro
    1355            1360                1365
Leu Arg Thr Val Asn Ala Ser Ser Lys Leu Tyr Tyr Ile Leu Pro
    1370            1375                1380
Asn Gly Val Glu Ile Arg Asn Ser Phe Gly Gln Asp Ile Gln Gly
    1385            1390                1395
Asn Thr Tyr Tyr Phe Asp Ala Arg Gly Glu Met Val Thr Ser Gln
    1400            1405                1410
```

```
Tyr Ile Ser Asp Asp Thr Gln Asn Ile Tyr Tyr Phe Asn Asn Asp
    1415                1420                1425

Gly Thr Met Ala Lys Gly Leu Ile Gln Leu Asn Thr Asn Leu Gln
    1430                1435                1440

Tyr Phe Gly Thr Asn Gly Ala Gln Leu Lys Gly Ala Tyr Val His
    1445                1450                1455

Asp Ile Ser Ser Asp Lys Trp Tyr Gln Phe Asp Ala Gly Ser Gly
    1460                1465                1470

Asn Gly Arg Gln Leu Thr Gln Arg Pro Asp Asp Val Asn Ala Asn
    1475                1480                1485

Asn Tyr Ile Ser Ile Asp Ser Ser Asn Ile Gly Val Asn Thr
    1490                1495                1500

Asp Tyr Thr Ala Tyr Ile Thr Ser Ser Leu Arg Glu Asp Gly Leu
    1505                1510                1515

Phe Ala Asn Ala Pro Tyr Gly Val Val Thr Lys Asp Gln Asn Gly
    1520                1525                1530

Asn Asp Leu Lys Trp Gln Tyr Ile Asn His Thr Lys Gln Tyr Glu
    1535                1540                1545

Gly Gln Gln Val Gln Val Thr Arg Gln Tyr Thr Asp Ser Lys Gly
    1550                1555                1560

Val Ser Trp Asn Leu Ile Thr Phe Ala Gly Gly Asp Leu Gln Gly
    1565                1570                1575

Gln Lys Leu Trp Val Asp Ser Arg Ala Leu Thr Met Thr Pro Phe
    1580                1585                1590

Lys Thr Met Asn Gln Ile Ser Phe Ile Ser Tyr Ala Asn Arg Asn
    1595                1600                1605

Asp Gly Leu Phe Leu Asn Ala Pro Tyr Gln Val Lys Gly Tyr Gln
    1610                1615                1620

Leu Ala Gly Met Ser Asn Gln Tyr Lys Gly Gln Gln Val Thr Ile
    1625                1630                1635

Ala Gly Val Ala Asn Val Ser Gly Lys Asp Trp Ser Leu Ile Ser
    1640                1645                1650

Phe Asn Gly Thr Gln Tyr Trp Ile Asp Ser Gln Ala Leu Asn Thr
    1655                1660                1665

Asn Phe Thr His Asp Met Asn Gln Lys Val Phe Val Asn Thr Thr
    1670                1675                1680

Ser Asn Leu Asp Gly Leu Phe Leu Asn Ala Pro Tyr Arg Gln Pro
    1685                1690                1695

Gly Tyr Lys Leu Ala Gly Leu Ala Lys Asn Tyr Asn Asn Gln Thr
    1700                1705                1710

Val Thr Val Ser Gln Gln Tyr Phe Asp Asp Gln Gly Thr Val Trp
    1715                1720                1725

Ser Gln Val Val Leu Gly Gly Gln Thr Val Trp Val Asp Asn His
    1730                1735                1740

Ala Leu Ala Gln Met Gln Val Arg Asp Thr Asn Gln Gln Leu Tyr
    1745                1750                1755

Val Asn Ser Asn Gly Arg Asn Asp Gly Leu Phe Leu Asn Ala Pro
    1760                1765                1770

Tyr Arg Gly Gln Gly Ser Gln Leu Ile Gly Met Thr Ala Asp Tyr
    1775                1780                1785

Asn Gly Gln His Val Gln Val Thr Lys Gln Gly Gln Asp Ala Tyr
    1790                1795                1800
```

```
Gly Ala Gln Trp Arg Leu Ile Thr Leu Asn Asn Gln Gln Val Trp
    1805                1810                1815

Val Asp Ser Arg Ala Leu Ser Thr Thr Ile Met Gln Ala Met Asn
    1820                1825                1830

Asp Asp Met Tyr Val Asn Ser Ser Gln Arg Thr Asp Gly Leu Trp
    1835                1840                1845

Leu Asn Ala Pro Tyr Thr Met Ser Gly Ala Lys Trp Ala Gly Asp
    1850                1855                1860

Thr Arg Ser Ala Asn Gly Arg Tyr Val His Ile Ser Lys Ala Tyr
    1865                1870                1875

Ser Asn Glu Val Gly Asn Thr Tyr Tyr Leu Thr Asn Leu Asn Gly
    1880                1885                1890

Gln Ser Thr Trp Ile Asp Lys Arg Ala Phe Thr Ala Thr Phe Asp
    1895                1900                1905

Gln Val Val Ala Leu Asn Ala Thr Ile Val Ala Arg Gln Arg Pro
    1910                1915                1920

Asp Gly Met Phe Lys Thr Ala Pro Tyr Gly Glu Ala Gly Ala Gln
    1925                1930                1935

Phe Val Asp Tyr Val Thr Asn Tyr Asn Gln Gln Thr Val Pro Val
    1940                1945                1950

Thr Lys Gln His Ser Asp Ala Gln Gly Asn Gln Trp Tyr Leu Ala
    1955                1960                1965

Thr Val Asn Gly Thr Gln Tyr Trp Ile Asp Gln Arg Ser Phe Ser
    1970                1975                1980

Pro Val Val Thr Lys Val Val Asp Tyr Gln Ala Lys Ile Val Pro
    1985                1990                1995

Arg Thr Thr Arg Asp Gly Val Phe Ser Gly Ala Pro Tyr Gly Glu
    2000                2005                2010

Val Asn Ala Lys Leu Val Asn Met Ala Thr Ala Tyr Gln Asn Gln
    2015                2020                2025

Val Val His Ala Thr Gly Glu Tyr Thr Asn Ala Ser Gly Ile Thr
    2030                2035                2040

Trp Ser Gln Phe Ala Leu Ser Gly Gln Glu Asp Lys Leu Trp Ile
    2045                2050                2055

Asp Lys Arg Ala Leu Gln Ala
    2060                2065

<210> SEQ ID NO 2
<211> LENGTH: 1392
<212> TYPE: PRT
<213> ORGANISM: Artificial Sequence
<220> FEATURE:
<223> OTHER INFORMATION: Truncated dextrane saccharase

<400> SEQUENCE: 2

Gln Thr Pro Val Gly Thr Thr Gln Ser Gln Gln Asp Leu Thr Gly Gln
1               5                   10                  15

Thr Gly Gln Asp Lys Pro Thr Thr Lys Glu Val Ile Asp Lys Lys Glu
                20                  25                  30

Pro Val Pro Arg Val Ser Ala Gln Asn Ala Gly Asp Leu Ser Ala Asp
            35                  40                  45

Ala Lys Thr Thr Lys Ala Asp Asp Lys Gln Asp Thr Gln Pro Thr Asn
        50                  55                  60

Ala Gln Leu Pro Asp Gln Gly Asn Lys Gln Thr Asn Ser Asn Ser Asp
65                  70                  75                  80
```

-continued

```
Lys Gly Val Lys Glu Ser Thr Thr Ala Pro Val Lys Thr Asp Val
                 85                  90                  95

Pro Ser Lys Ser Val Ala Pro Glu Thr Asn Thr Ser Ile Asn Ala Ser
            100                 105                 110

Asp Ala Ile Ser Lys Ser Gln Glu Lys Gln Phe Glu Lys Ala Pro Asp
            115                 120                 125

Ser Val Pro Glu Thr Ile Thr Gly Gly Arg Tyr Ser Leu Lys Asp Gly
            130                 135                 140

Tyr Tyr Val Tyr Leu Asp Lys Gln Gly Lys Gln Val Val Gly Pro Lys
145                 150                 155                 160

Asn Ile Asp Asn His Leu Gln Tyr Phe Asp Glu Thr Thr Gly Lys Gln
                165                 170                 175

Val Lys Gly Asp Phe Arg Ser Val Asn Gly Lys Arg Ile Tyr Phe Asn
            180                 185                 190

Ala Asn Leu Gly Tyr Ala Asp Asp Tyr Thr Thr Asp Val Ala Gly Lys
            195                 200                 205

Leu Val Gly Tyr Asp Ser Asn Gly Asn Gln Val Lys Ala Gly Tyr Val
            210                 215                 220

Thr Asn Ser Gln Gly Lys Thr Tyr Tyr Phe Asn Asn Gln Gly Glu Ala
225                 230                 235                 240

Ile Ile Gly Leu Lys Thr Asp Asn Asn Lys Thr Gln Tyr Phe Gly Pro
                245                 250                 255

Asp Gly Ala Gln Val Lys Gly Ala Phe Gln Gln Val Asn Gly Lys Asn
            260                 265                 270

Ile Tyr Phe Asp Ala Gln Thr Gly Tyr Ala Arg Gln Asn Val Gly Phe
            275                 280                 285

Leu Asp Gly Thr Ala Lys Gly Phe Asp Glu Gln Gly Asn Gln Ile Lys
            290                 295                 300

Ser Gly Ile Ala Thr Asp Leu Ser Gly Asn Val Tyr Tyr Phe Asp Ala
305                 310                 315                 320

Ser Gly Lys Met Leu Thr Gly Val Gln Asn Ile Asp Gly Lys Lys Tyr
                325                 330                 335

Tyr Phe Asp Glu Gln Gly His Arg Arg Arg Asn Tyr Ala Gly Val Phe
            340                 345                 350

Asn Asn Glu Phe Ile Tyr Phe Gly Leu Asp Gly Val Gly Gln Ser Ala
            355                 360                 365

Ile Glu Tyr Gln Phe Glu Lys Gly Leu Thr Ser Gln Asn Ser Val Ala
            370                 375                 380

Thr Ser His Asn Ala Ala Lys Ser Tyr Asp Thr Lys Ser Phe Thr Asn
385                 390                 395                 400

Val Asp Gly Phe Leu Thr Ala Asn Ser Trp Tyr Arg Pro Thr Asp Ile
            405                 410                 415

Leu Arg Asn Gly Thr Lys Trp Glu Pro Ser Thr Glu Thr Asp Phe Arg
            420                 425                 430

Pro Leu Leu Met Thr Trp Trp Pro Asp Lys Glu Val Gln Ala Asn Tyr
            435                 440                 445

Leu Asn Tyr Met Ser Ala Leu Gly Leu Gly Asp Gln Lys Ile Tyr Thr
            450                 455                 460

Gly Ala Ser Ser Gln Leu Asp Leu Asn Asn Ala Ala Leu Ile Val Gln
465                 470                 475                 480

Glu Ala Ile Glu Lys Lys Ile Ser Leu Glu Lys Ser Thr Lys Trp Leu
                485                 490                 495

Asp Asp Ser Ile Lys Ser Phe Ile Lys Ser Lys Arg Lys Asp Ile Gln
```

```
                    500                 505                 510
Gly Asn Leu Val Asp Thr Asn Pro Gly Trp Thr Ile Asp Ser Glu Thr
                515                 520                 525
Gly Ser Thr Asn His Leu Gln Asn Gly Ala Phe Ile Phe Thr Asn Ser
            530                 535                 540
Pro Leu Val Pro Glu Ala Asn Ala Ala Glu Gly Asn Arg Leu Ile Asn
545                 550                 555                 560
Arg Thr Pro Ser Gln Gln Thr Gly Asn His Ile Ser Tyr Ala Ser Gln
                565                 570                 575
Pro Tyr Ser Gly Asp Asp Trp Gly Tyr Glu Leu Leu Gly Asn Asp
            580                 585                 590
Val Asp Asn Ser Asn Pro Ile Val Gln Ala Glu Gln Leu Asn Trp Ile
            595                 600                 605
His Tyr Leu Met Asn Phe Gly Thr Ile Thr Ala Pro Gln Asp Pro Asp
            610                 615                 620
Ala His Leu Ala Asn Phe Asp Ser Ile Arg Ile Asp Ala Val Asp Asn
625                 630                 635                 640
Val Asp Ala Asp Leu Leu Gln Ile Ala Gly Asp Tyr Phe Lys Ala Ala
                645                 650                 655
Tyr Gln Val Gly Glu Asn Asp Lys Asn Ala Asn Gln His Ile His Ile
                660                 665                 670
Leu Glu Asp Trp Ser Pro Asn Asp Val Trp Tyr Asn Gln Gln Val Asn
            675                 680                 685
Gly Asn Ser Gln Leu Thr Met Asp Ala Thr Met Gln Asn Gln Leu Leu
            690                 695                 700
Ala Ser Leu Thr Arg Pro Ile Thr Ser Arg Asp Ser Met Lys Ser Phe
705                 710                 715                 720
Thr Lys Asp Ala Leu Leu Val His Arg Thr Ala Asp Asn Ser Tyr Asn
                725                 730                 735
Gln Ala Val Pro Asn Tyr Ser Phe Ile Arg Ala His Asp Ser Glu Val
            740                 745                 750
Gln Thr Ile Ile Ala Lys Ile Ile Ser Asp Lys His Pro Asp Leu Tyr
            755                 760                 765
Pro Thr Val Asp Lys Ala Leu Leu Ala Lys Asp Ser Ala Leu Tyr Asp
            770                 775                 780
Glu Ala Phe Thr Glu Tyr Asn Ala Asp Met Gln Lys Ile Ser Ser Gln
785                 790                 795                 800
Lys Gln Tyr Thr His Asn Asn Met Pro Ser Ala Tyr Ala Ile Leu Leu
                805                 810                 815
Thr Asn Lys Asp Thr Val Pro Arg Val Tyr Tyr Gly Asp Leu Phe Thr
            820                 825                 830
Asp Asn Gly Glu Tyr Met Ala Asn Lys Thr Pro Tyr Tyr Asp Ala Ile
            835                 840                 845
Thr Ser Leu Leu Thr Ala Arg Thr Lys Phe Val Ser Gly Gly Gln Ser
            850                 855                 860
Leu Ser Val Asp Lys Asn Asp Val Leu Thr Ser Val Arg Tyr Gly Lys
865                 870                 875                 880
Gly Ala Leu Ser Ala Thr Asp Asn Gly Ser Ser Asp Thr Arg Asn Gln
                885                 890                 895
Gly Ile Gly Val Ile Val Ser Asn Asn Pro Asn Leu Asp Leu Asn Asn
                900                 905                 910
Asp Lys Val Thr Leu Ser Met Gly Ile Ser His Ala His Gln Ala Tyr
            915                 920                 925
```

```
Arg Pro Leu Leu Leu Thr Asn Ser Gln Gly Ile Val Ala Tyr Ala Thr
    930                 935                 940

Asp Ser Glu Val Pro Gln Asn Leu Tyr Lys Thr Thr Asn Asp Lys Gly
945                 950                 955                 960

Glu Leu Thr Phe Asp Ala Ser Glu Ile Lys Gly Tyr Asp Thr Val Gln
                965                 970                 975

Thr Ser Gly Tyr Leu Ala Val Trp Val Pro Val Gly Ala Ser Asp Glu
            980                 985                 990

Gln Asp Ala Arg Thr Ile Ala Ser Thr Glu Lys Asn Asn Gly Asn Ser
                995                 1000                1005

Val Tyr His Ser Asn Ala Ala Leu Asp Ser Gln Leu Ile Tyr Glu
    1010                1015                1020

Gly Phe Ser Asn Phe Gln Thr Val Pro Ser Lys Asn Ala Ser Ala
    1025                1030                1035

Asp Glu Tyr Ala Asn Val Ile Ile Ala Lys His Ala Ala Asp Phe
    1040                1045                1050

Asn Lys Trp Gly Val Thr Ser Phe Gln Met Ala Pro Gln Tyr Arg
    1055                1060                1065

Ser Ser Thr Asp Gly Ser Phe Leu Asp Ala Val Asp Thr Val Gln
    1070                1075                1080

Asn Gly Tyr Ala Phe Thr Asp Arg Tyr Asp Leu Gly Phe Asn Ala
    1085                1090                1095

Ala Asp Gly Ser Lys Asn Pro Thr Lys Tyr Gly Thr Asp Glu Asp
    1100                1105                1110

Leu Arg Asn Ala Ile Lys Ser Leu His Ala Gln Lys Thr Tyr Asp
    1115                1120                1125

Gly Ser Ser Ile Gln Val Met Ala Asp Phe Val Pro Asp Gln Leu
    1130                1135                1140

Tyr Asn Met Pro Leu Glu Gln Ala Val Ser Val Ile Arg Thr Asp
    1145                1150                1155

Lys Tyr Gly Val Asn Ser Glu Asn Pro Asp Ile Gln Asn Ile Ile
    1160                1165                1170

Tyr Ala Ala Asn Ile Lys Ser Ser Gly Thr Asp Tyr Gln Ser Ile
    1175                1180                1185

Tyr Gly Gly Lys Tyr Leu Ala Glu Leu Gln Lys Asn Pro Leu Phe
    1190                1195                1200

Lys Ser Leu Phe Asp Arg Ile Gln Ile Ser Thr Lys Lys Thr Ile
    1205                1210                1215

Asp Pro Asn Thr Arg Ile Thr Gln Trp Ser Ala Lys Tyr Phe Asn
    1220                1225                1230

Gly Ser Asn Ile Gln Gly Lys Gly Ile Asn Tyr Val Leu Lys Asp
    1235                1240                1245

Trp Ala Ser Asn Lys Tyr Phe Asn Val Ser Ser Asn Asp Asp Met
    1250                1255                1260

Tyr Ser Arg Leu Pro Lys Gln Leu Met Asn Gln Glu Ser Asn Thr
    1265                1270                1275

Gly Phe Ile Val Asp Asp Ile Gly Val Lys Tyr Tyr Ser Ile Ser
    1280                1285                1290

Gly Tyr Gln Ala Lys Asn Thr Phe Val Glu Asp Gly Asn Gly Glu
    1295                1300                1305

Trp Tyr Tyr Phe Asp Asn Asp Gly Tyr Met Val Lys Ser Thr Glu
    1310                1315                1320
```

```
Glu Ser Gly Pro Leu Arg Thr Val Asn Ala Ser Ser Lys Lys Tyr
    1325            1330                1335

Tyr Ile Leu Pro Asn Gly Val Glu Ile Arg Asn Ser Phe Gly Gln
    1340            1345                1350

Asp Ile Gln Gly Asn Thr Tyr Tyr Phe Asp Ala Arg Gly Glu Met
    1355            1360                1365

Val Thr Ser Gln Tyr Ile Ser Asp Asp Thr Gln Asn Ile Tyr Tyr
    1370            1375                1380

Phe Asn Asn Asp Gly Thr Met Ala Lys
    1385            1390

<210> SEQ ID NO 3
<211> LENGTH: 33
<212> TYPE: DNA
<213> ORGANISM: Artificial Sequence
<220> FEATURE:
<223> OTHER INFORMATION: primer

<400> SEQUENCE: 3
caccatgaaa ataaaagaaa caattacccg aaa                              33

<210> SEQ ID NO 4
<211> LENGTH: 26
<212> TYPE: DNA
<213> ORGANISM: Artificial Sequence
<220> FEATURE:
<223> OTHER INFORMATION: primer

<400> SEQUENCE: 4
aagcttgcaa agcacgctta tcaatc                                       26

<210> SEQ ID NO 5
<211> LENGTH: 28
<212> TYPE: DNA
<213> ORGANISM: Artificial Sequence
<220> FEATURE:
<223> OTHER INFORMATION: primer

<400> SEQUENCE: 5
cacccaaacg ccggttggta caacacag                                     28

<210> SEQ ID NO 6
<211> LENGTH: 24
<212> TYPE: DNA
<213> ORGANISM: Artificial Sequence
<220> FEATURE:
<223> OTHER INFORMATION: primer

<400> SEQUENCE: 6
ttttgccatc gtaccatcgt tatt                                         24
```

PROTEIN WITH DEXTRAN-SACCHARASE ACTIVITY, AND USES

STATEMENT REGARDING SEQUENCE LISTING

The Sequence Listing associated with this application is provided in text format in lieu of a paper copy, and is hereby incorporated by reference into the specification. The name of the text file containing the Sequence Listing is 480373_402USPC_SEQUENCE_LISTING.txt. The text file is 30.9 KB, was created on Jan. 25, 2017, and is being submitted electronically via EFS-Web.

A subject of the invention is a protein with dextransucrase activity derived from the *Leuconostoc citreum* strain NRRL B-1299, especially a truncated protein with dextransucrase activity. The invention also relates to a process for synthesizing dextrans by means of such a protein with dextransucrase activity, and also the dextrans synthesized.

For further clarity in the remainder of the text, the term "dextransucrase" may sometimes be used to denote a protein with dextransucrase activity.

The glucansucrases of bacterial origin are α-transglucosylases belonging to the families 13 and 70 of the glycoside hydrolases. These enzymes generally catalyse the synthesis of α-glucans of high molar mass ($10^6$-$10^9$ g·mol$^{-1}$) from sucrose. They may also synthesize oligosaccharides or glucoconjugates by transglucosylation reaction on exogenous acceptors of varied natures. Glucansucrases have different product specificities, both in terms of the nature of the glycosidic bonds synthesized (α-1,2; α-1,3; α-1,4 or α-1,6) and their organisation, and in terms of the size of the products formed.

Generally speaking, glucansucrases are naturally produced by lactic bacteria, for example of the genera *Leuconostoc*, *Lactobacillus*, *Streptococcus* or *Weissela* sp.

Among the glucansucrases, dextransucrases produce dextran, generally having at least 50% α-1,6 glycosidic bonds in the main chain, and optionally α-1,2, α-1,3 and/or α-1,4 branching. The content of branching and the spatial arrangement thereof vary according to the producing enzyme.

Dextrans and dextran derivatives have a growing number of industrial applications, often dependent on their molar masses.

Unless indicated otherwise, "molar mass" or "average molar mass" means, in the present invention, the weight-average molar mass, expressed either as g·mol$^{-1}$ or Da.

Dextrans of low or medium molar mass (generally ranging from $10^3$ to $7\times10^4$ g·mol$^{-1}$) are especially used for analytical applications, in the medical field, for example as blood plasma extender, by virtue of their weakly antigenic character and their low viscosity in saline solution, for ophthalmic solutions, iron transporter, anticoagulant (after functionalization), in the prevention of postoperative shock, in the treatment of burns or in the reduction of risks of thrombosis or embolisms, etc.

These dextrans of low or medium molar mass are generally produced by acid hydrolysis, followed by fractionation by means of organic solvents. However, these chemical processes are often costly, barely profitable and polluting.

Alternative processes have therefore been developed in order to improve the production of dextrans of low or medium molar mass.

Thus, U.S. Pat. No. 5,229,277 describes a process for synthesizing dextrans of low molar mass employing the use of *Leuconostoc mesenteroides* and a mutant strain of *Lipomyces starkeyi* ATCC 74054. This process, in addition to requiring the use of two microorganisms, necessitates specific culture conditions and precise durations and temperatures for the dextranase activity identified in *Lipomyces starkeyi* ATCC 74054 to reduce the molar mass of the dextrans synthesized by *Leuconostoc mesenteroides*. The dextran polymers produced have a molar mass of between $4\times10^4$ and $1.5\times10^5$ Da.

Patent application EP2365084 describes a process for synthesizing dextrans of controlled molar mass. These α-glucans are produced directly by truncated forms of the glucansucrase DsrS, derived from *Leuconostoc mesenteroides* NRRL B-512 F, from sucrose, with the optional addition of an exogenous acceptor. A DsrS Core ΔA variant is particularly beneficial for the production of dextrans of average molar mass of $1\times10^4$ Da.

However, the synthesis must be carried out at low temperatures (preferentially at 10° C.) in order to maximize yields. Moreover, the enzyme does not have high catalytic efficiency, and approximately 48 hours of synthesis are necessary to achieve total sucrose consumption.

It is also possible to promote the production of dextrans of low molar mass by increasing the initial substrate concentration. However, it has often been demonstrated with this method that the dextran produced was quite often polydisperse, and that the synthesis of polymers of high molar mass was not completely suppressed.

There is therefore still a need to produce dextrans having a low molar mass, especially barely polydisperse dextrans.

An aim of the invention was also to provide linear dextrans. Indeed, such dextrans are useful in numerous fields, especially for medical applications. This is because it has been shown that dextrans having a high content of α-1,6 bonds (and hence the most linear) are those which lead to the least allergenic reactions (1, 2).

Another aim of the invention was also to provide a process for producing such dextrans enzymatically and not chemically, and simply, quickly and precisely, only requiring the use of a single microorganism.

Another aim of the invention was to be able to very precisely control the molar mass of a synthesized dextran, especially by means of readily controllable reaction parameter(s).

It was thus to the inventors' merit to have discovered that a protein with dextransucrase activity derived from the *Leuconostoc citreum* strain NRRL B-1299 enables the synthesis of dextrans of precisely controllable molar mass, without requiring restrictive enzymatic reactions, directly from sucrose and without adding exogenous acceptor or other enzyme(s).

Such a protein has the sequence SEQ ID NO: 1 as amino acid sequence. The protein only has a maximum identity of 62% over 100% of its sequence with the alternansucrase of *Leuconostoc mesenteroides* LBAE C11, the sequence of which is available in databases under the Genbank accession number WP_004904957.1. Compared to other putative glucansucrase sequences which may be identified following campaigns for sequencing bacterial genomes, this percentage identity is rather low.

The protein with dextransucrase activity, having the sequence SEQ ID NO: 1 as amino acid sequence, referred to as DsrM, of molar mass 229 kDa, is composed of 2065 amino acids, having the DED catalytic triad, and the 4 conserved motifs customarily described in enzymes of glycoside hydrolase family 70. The conserved protein motifs of the catalytic core (I to IV) have thus been identified from position 1177 to position 1183 for motif I, from position 673 to position 683 for motif II, from position 710 to position 721 for motif III and from position 785 to position 799 for motif IV. In comparison with the protein sequence of glucansucrase GTF-180, the five structural domains conventionally described for the glucansucrases (A, B, C, IV and V) (3) may be identified in the primary structure of the protein with dextransucrase activity of amino acid sequence SEQ ID NO: 1 (FIG. 1).

The function-preserving variants of the protein with dextransucrase activity of amino acid sequence SEQ ID NO: 1 are also included in the present application.

"Function-preserving variant" refers to a variant in which one or more given amino acid residue(s) in a protein has (have) been modified or deleted or inserted without this altering the overall conformation and the enzymatic activity of the protein with dextransucrase activity. The enzymatic activity of a dextransucrase variant may be tested according to techniques known to those skilled in the art, for example by the dinitrosalicylic (DNS) method of Sumner and Howell (4) or by HPLC analysis.

Preferably, such a function-preserving variant is a protein with dextransucrase activity, the amino acid sequence of which has at least 80%, preferably 85%, more preferably still 90%, more preferably still 95%, more preferably still 98% identity to the amino acid sequence SEQ ID NO: 1.

Advantageously, the modification(s) relate to the non-sensitive parts of the enzyme and therefore especially do not relate to the zone from position 563 to position 1282 of the amino acid sequence SEQ ID NO: 1, corresponding to the catalytic triad and to the domains A, B and C.

Preferably, the modification(s) especially do not relate to the zone from position 563 to position 1282 of the amino acid sequence SEQ ID NO: 1 and also the zones from position 1316 to 1433 (C-terminal part of the domain V) of the amino acid sequence SEQ ID NO: 1.

More preferably still, the modification(s) especially do not relate to the zone from position 563 to position 1282 of the amino acid sequence SEQ ID NO: 1, the zones from position 1316 to 1433 of the amino acid sequence SEQ ID NO: 1, and the zones from position 174 to 421 of the amino acid sequence SEQ ID NO: 1.

Indeed, the sequences from positions 174 to 421, then from 1316 to 1433 comprises repeat units (YG repeats) generally described in this family as having an affinity for glucan and hence playing a role in the size of the products formed, and also in the catalytic activity of the enzyme (3).

More preferably still, the modification(s) especially do not relate to the zone from position 563 to position 1282 of the amino acid sequence SEQ ID NO: 1, the zones from position 1316 to 1433 of the amino acid sequence SEQ ID NO: 1, and the zones from position 42 to 421 of the amino acid sequence SEQ ID NO: 1.

Figure 2:
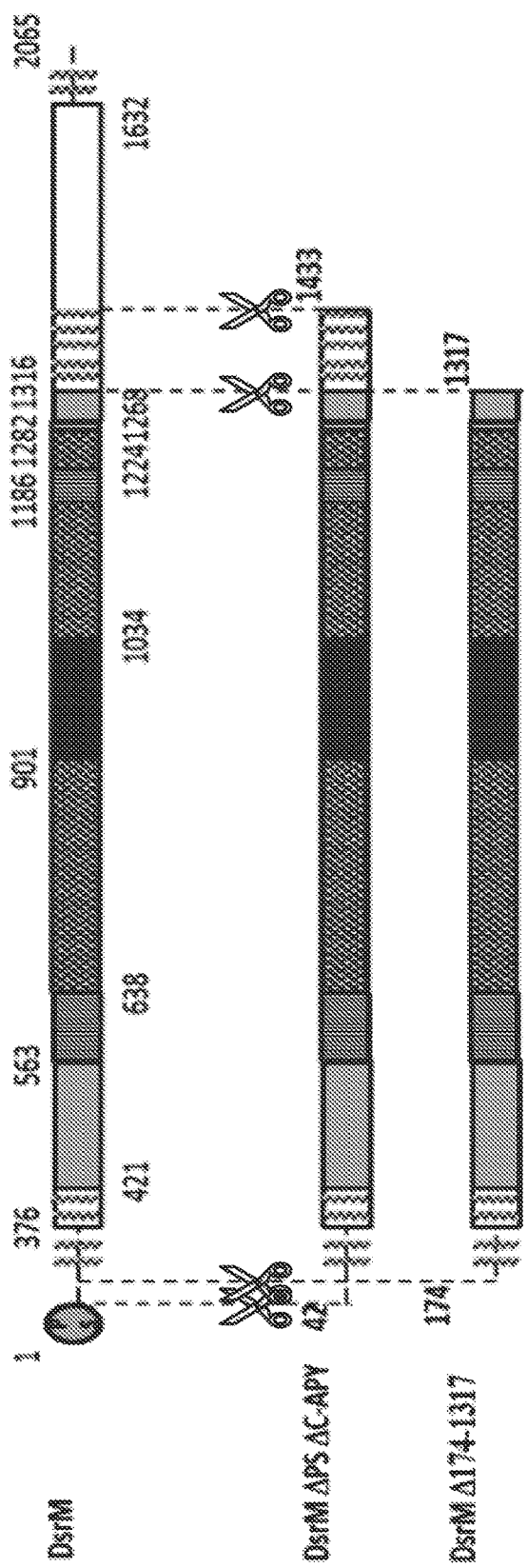

Thus, it was demonstrated during truncation assays of the dextransucrase of the amino acid sequence SEQ ID NO: 1 that the deletion of the amino acids from position 1434 to 2065 of the C-terminal domain V, especially including all the "APY motifs" did not have an impact on the activity and specificity of the enzyme (cf. FIG. 2, truncated dextransucrase DsrM ΔPS ΔC-APY).

On the other hand, it was demonstrated that the deletion of the amino acids from position 1 to 174 and from position 1317 to 2065 of the amino acid sequence SEQ ID NO: 1 (domain V at the C-terminal end), caused the enzyme to lose its activity (cf. FIG. 2, truncated dextransucrase DsrM Δ174-1317).

Those skilled in the art are able to determine the function-preserving variants, especially in light of these elements.

Thus, a subject of the invention is a protein with dextransucrase activity, having the sequence SEQ ID NO: 1 as amino acid sequence, or comprising at least 80%, preferably 85%, more preferably still 90%, more preferably still 95%, more preferably still 98% identity at positions 563 to 1282 of the amino acid sequence SEQ ID NO: 1, preferably at positions 563 to 1282 and 1316 to 1433 of the amino acid sequence SEQ ID NO:1, more preferably still at positions 563 to 1282, 1316 to 1433 and 174 to 421 of the amino acid sequence SEQ ID NO:1. more preferably still at positions 563 to 1282, 1316 to 1433 and 42 to 421 of the amino acid sequence SEQ ID NO:1.

According to a specific embodiment, a function-preserving variant consists of a truncated form of a protein with dextransucrase activity as defined above and which conserves the dextransucrase enzymatic activity.

Such a truncated form preferably comprises less than 2065 amino acids, preferably less than 1600 amino acids, more preferably still less than 1450 amino acids. Very preferentially, such a truncated form comprises 1392 amino acids.

According to a specific embodiment, such a truncated form of the protein with dextransucrase activity of the amino acid sequence SEQ ID NO: 1 has the sequence SEQ ID NO:2 as amino acid sequence. This specific truncated form is referred to as DsrM ΔPS ΔC-APY.

The amino acid sequence SEQ ID NO: 2 is identical to the amino acid sequence SEQ ID NO: 1 from position 42 to position 1433, and positions 1 to 41 and 1434 to 2065 of the amino acid sequence SEQ ID NO:1 have been deleted. As mentioned above, it has thus been demonstrated that deleting these amino acids, including especially all of the "APY motifs", does not have an impact on the activity and specificity of the enzyme.

Moreover, the protein with dextransucrase activity of amino acid sequence SEQ ID NO: 2 does not exceed 54% identity, and 68% similarity, with the protein sequences of DsrS and its variants DsrS vardel Δ3, DsrS vardel Core and DsrS Core ΔA (cf. patent application EP2365084).

The function-preserving variants of the protein with dextransucrase activity of amino acid sequence SEQ ID NO: 2 are also included in the present application and are defined in the same way as above.

Thus, preferably, the modification(s) may relate to the non-sensitive parts of the enzyme and therefore especially do not relate to the zone from position 522 to position 1241 of the amino acid sequence SEQ ID NO: 2, corresponding to the catalytic triad and to the domains A, B and C.

Preferably, the modification(s) especially do not relate to the zone from position 522 to position 1241 of the amino acid sequence SEQ ID NO: 2 and also the zones from position 1275 to 1392 (C-terminal part of the domain V) of the amino acid sequence SEQ ID NO: 2.

More preferably still, the modification(s) especially do not relate to the zone from position 522 to position 1241 of the amino acid sequence SEQ ID NO: 2, the zones from position 1275 to 1392 of the amino acid sequence SEQ ID NO: 2, and the zones from position 133 to 380 of the amino acid sequence SEQ ID NO: 2.

More preferably still, the modification(s) especially do not relate to the zone from position 522 to position 1241 of the amino acid sequence SEQ ID NO: 2, the zones from position 1275 to 1392 of the amino acid sequence SEQ ID NO: 2, and the zones from position 1 to 380 of the amino acid sequence SEQ ID NO: 2.

Thus, a subject of the invention relates to a protein with dextransucrase activity, having the sequence SEQ ID NO: 2 as amino acid sequence, or comprising at least 80%, preferably 85%, more preferably still 90%, more preferably still 95%, more preferably still 98% identity at positions 522 to 1241 of the amino acid sequence SEQ ID NO: 2, preferably at positions 522 to 1241 and 1275 to 1392 of the amino acid sequence SEQ ID NO:2, more preferably still at positions 522 to 1241, 1275 to 1392 and 133 to 380 of the amino acid sequence SEQ ID NO:2, more preferably still at positions 522 to 1241, 1275 to 1392 and 1 to 380 of the amino acid sequence SEQ ID NO: 2.

Hereinafter, the term "protein with dextransucrase activity of amino acid sequence SEQ ID NO: 2" (or "dextransucrase with the amino acid sequence SEQ ID NO: 2") relates equally to the protein with dextransucrase activity of amino acid sequence SEQ ID NO: 2 and to its function-preserving variants. According to a specific embodiment, it is just the protein with dextransucrase activity of the amino acid sequence SEQ ID NO: 2.

The exceptional functional properties of a dextransucrase according to the invention have been demonstrated by the inventors.

A protein with dextransucrase activity according to the invention is exclusively specific for polymerization via α-1,6-type glycosidic bonds, and moreover is an excellent polymerase. Indeed, as demonstrated in the experimental section, chromatographic analyses carried out following synthesis of dextran from 100 g·l$^{-1}$ of sucrose show that approximately 85% and 81% of the glucosyl units derived from the sucrose are used for the production of the polymer during the use, respectively, of a dextransucrase with the amino acid sequence SEQ ID NO: 2 and of a dextransucrase with the amino acid sequence SEQ ID NO: 1.

In addition, a protein with dextransucrase activity according to the invention has an optimal operating temperature of between 30° C. and 45° C., and has an optimal pH of between 4 and 7, more specifically between 4.5 and 5.75 for a protein with dextransucrase activity with the amino acid sequence SEQ ID NO: 2, and between 5 and 7 for a protein with dextransucrase activity with the amino acid sequence SEQ ID NO: 1.

A dextransucrase according to the invention thus offers a broad usage range in terms of pH and of temperatures. The enzyme especially conserves more than 80% of its activity over a broad temperature range, especially up to 45° C., which is very rare in enzymes of glycoside hydrolase family 70. Now, carrying out the synthesis of dextrans at high temperatures, for example approximately 45° C., makes it possible to limit certain microbial contaminations. This broad usage range consequently makes the dextransucrase according to the invention very attractive for industrial uses.

According to a specific embodiment, a protein with dextransucrase activity according to the invention may be prepared by known techniques of genetic recombination.

Those skilled in the art will know how to use molecular biology techniques and will know how to choose a suitable expression system according to the techniques known to them. Reference may be made here to the experimental results below.

The term "expression system" comprises a host cell and a vector compatible under appropriate conditions, that is to say conditions enabling the expression of the gene encoding the protein of interest, borne by the vector and introduced into the host cell. Typically, the nucleic acid sequence encoding a protein with dextransucrase activity according to the invention may be inserted in a suitable expression vector which will then be introduced into an adequate prokaryotic or eukaryotic host cell.

Any suitable expression vector known to those skilled in the art may be used according to the invention. An expression vector is typically a plasmid, a cosmid, an episome, an artificial chromosome, a phage or a viral vector. The expression vector used is advantageously pET-53-DEST, pET-55-DEST, pET-60-DEST or pBAD-DEST49.

Typically, the nucleic acids of the present invention may be expressed in prokaryotic or eukaryotic host cells. As nonlimiting examples of prokaryotic host cell strains, mention may be made of strains such as *Escherichia coli, Bacillus subtilis, Salmonella typhimurium* or strains of the genus *Pseudomonas, Streptomyces* and *Staphylococcus*. As nonlimiting examples of eukaryotic host cell strains, mention may be made of strains such as the parasites Apicomplexan (*Plasmodia, Toxoplasma, Cryptosporidia*) *Leishmania* or *Trypanosoma*, or yeast cells such as *Saccharomyces* sp. For instance *Saccharomyces cerevisiae* or *pombe, Pichia pastoris* etc.

Prokaryotic host cells are preferentially used. According to one advantageous embodiment, the cells used for the expression of the nucleic acids of the present invention are *Escherichia coli* and more preferentially still the strains are chosen from TOP10, BL21-AI, BL21 Star DE3, and Arctic Express DE3.

According to a specific embodiment, in which the dextransucrase according to the invention is a truncated dextransucrase as defined above, the nucleic acid sequence encoding a dextransucrase with the amino acid sequence SEQ ID NO: 2 as described above is inserted into a pET-55-DEST expression vector, then introduced into a prokaryotic host cell of *Escherichia coli* BL21 Star DE3 type. This embodiment makes it possible to produce dextransucrase, and makes it possible to obtain approximately 10 000 Units of enzymatic activity per liter of culture.

A dextransucrase according to the invention may be prepared by culturing host cells containing a nucleic acid sequence encoding a dextransucrase according to the invention, under conditions enabling the expression of a dextransucrase, and by isolating said dextransucrase from the culture medium according to techniques known to those skilled in the art.

Such dextransucrases may then be purified by any purification technique known to those skilled in the art, for example by precipitation, ion exchange chromatography, affinity chromatography, hydrophobic interaction chromatography, gel filtration, reversed-phase HPLC chromatography, etc. According to a preferential embodiment, the dextransucrase obtained by culturing host cells is purified by affinity chromatography.

Advantageously, a dextransucrase according to the invention may also be immobilized by techniques known to those skilled in the art, for example by the formation of ionic and/or hydrophobic bonds between the support and the protein (adsorption), formation of covalent bonds between the support and the protein, inclusion of the protein in the support or encapsulation of the protein in the support. The immobilization of a dextransucrase according to the invention constitutes a particularly advantageous embodiment according to the invention, as will be seen below.

Due to their noteworthy dextransucrase properties, the proteins with dextransucrase activity according to the invention also enable the synthesis of dextrans. Those skilled in the art will know to adapt the experimental conditions to be applied to have optimized production of dextran. Generally, the dextransucrase must be incubated in a synthesis medium containing sucrose.

Consequently, one subject of the invention relates to a process for synthesizing dextrans, in which:

sucrose is provided in a synthesis medium, a dextransucrase according to the invention is placed in contact with said sucrose in said synthesis medium, to form dextrans, the dextrans obtained are optionally isolated.

Advantageously, the pH used for the synthesis process is between 4 and 7, preferably between 4.5 and 5.75 for a dextransucrase with the amino acid sequence SEQ ID NO: 2, and between 5 and 7 for a dextransucrase with the amino acid sequence SEQ ID NO: 1. The pH used for the manufacturing process is approximately 5.75.

The synthesis medium may be any medium known to those skilled in the art and suitable for the synthesis of dextrans according to the invention. The synthesis medium is preferably a liquid medium comprising a solvent. Those skilled in the art will especially be able to use any solvent enabling the pH desired for the synthesis to be achieved. Thus, said solvent may, for the purposes of illustration, be chosen from water, or a suitable buffer solution (for example sodium acetate).

Those skilled in the art will know how to adapt the duration of the synthesis, in particular as a function of the amount of protein with dextransucrase activity added to the synthesis medium and as a function of the temperature. Thus, a longer synthesis duration will be necessary when high concentrations of sucrose are used in the synthesis medium, for example of the order of 400 g·l$^{-1}$ to 600 g·l$^{-1}$. Typically, at an enzyme concentration of 1 U·ml$^{-1}$, the synthesis is carried out for a duration of between 4 hours and 24 hours, preferably of between 8 hours and 16 hours, preferably for a duration of approximately 14 hours.

Particularly advantageously, broad ranges of temperature and initial substrate concentration may be used, which also enable the precise control of the molar mass of the dextrans obtained.

The sucrose concentration in the synthesis medium may generally be between 50 and 600 g·l$^{-1}$, preferably between 50 and 400 g·l$^{-1}$. Typically, sucrose concentrations in the synthesis medium of between 50 and 200 g·l$^{-1}$ for dextrans with a higher molar mass will be used, and sucrose concentrations in the synthesis medium of between 200 and 600 g·l$^{-1}$, preferably between 200 and 400 g·l$^{-1}$, will be used for dextrans with a lower molar mass. Indeed, it is already known that the average molar mass of the synthesized dextran will be liable to be higher when using a low initial sucrose concentration in the synthesis medium.

Moreover, the synthesis may generally be carried out at a temperature of between 20° C. and 50° C., preferably of between 25° C. and 45° C. As mentioned above, use of the enzyme over a broad range of temperatures, especially up to 45° C., is very rare in enzymes of glycoside hydrolase family 70. Now, carrying out the synthesis of dextrans at high temperatures, for example approximately 45° C., makes it possible to limit certain microbial contaminations.

Moreover, it has been shown in previous studies that an increase in the temperature made it possible to obtain dextrans of higher molar mass (5, 6). Now, it has been demonstrated here, surprisingly, that, on the contrary, during the synthesis of dextrans by means of a dextransucrase according to the invention, a reduction in the temperature caused dextrans of higher molar masses.

Typically, temperatures between 20° C. and 35° C. will be used, preferably between 25° C. and 35° C., for dextrans with a higher molar mass, and temperatures between 35° C. and 50° C., preferably between 35° C. and 45° C. will be used for dextrans with a lower molar mass. The reaction temperature thus has a large influence on the molar mass of the products formed by the enzyme of the present invention.

Moreover, preference will be given to using high sucrose concentrations, especially from 200 to 600 g·l$^{-1}$, preferably between 200 and 400 g·l$^{-1}$, for reactions carried out at high temperatures, especially greater than or equal to 45° C.

The molar mass of a synthesized dextran may be very precisely controlled by the choice of the temperature and the sucrose concentration, which is particularly advantageous as this makes it possible to very precisely provide a broad range of dextrans in terms of molar mass.

Indeed, as demonstrated in the experimental section, here, surprisingly, a linear variation in the molar mass of the dextrans obtained is observed when the synthesis temperature (or the sucrose concentration) is fixed and the sucrose concentration (or the synthesis temperature) is varied. This very surprising result which, as far as the inventors know, has never been observed before, is a particularly advantageous characteristic of the invention in that it makes it possible to obtain, via temperatures ranging from 20° C. to 50° C. and initial sucrose concentrations ranging from 50 g·l$^{-1}$ to 600 g·l$^{-1}$, dextrans with a molar mass ranging from 2×10$^3$ to 40×10$^3$ g·l$^{-1}$.

According to a specific embodiment of the invention according to which a dextransucrase with the amino acid sequence SEQ ID NO: 2 is used, the dextrans have a molar mass ranging from 7×10$^3$ to 25×10$^3$ g·mol$^{-1}$.

Thus, by way of example, by fixing the temperature at 25° C., the process for synthesizing dextrans according to the invention makes it possible to obtain, from a dextransucrase with the amino acid sequence SEQ ID NO: 2, a dextran of average molar mass 25×10$^3$ g·mol$^{-1}$ from 50 g·l$^{-1}$ of sucrose and a dextran of average molar mass 8×10$^3$ g·mol$^{-1}$ from 400 g·l$^{-1}$ of sucrose. Similarly, at an initial sucrose concentration fixed at 200 g·l$^{-1}$, it is possible to obtain a dextran, the average molar mass of which is 17×10$^3$ g·mol$^{-1}$ at 25° C. and a dextran, the average molar mass of which is 8.5×10$^3$ g·mol$^{-1}$ at 45° C.

Thus, a subject of the invention relates to a dextran able to be obtained by the process as described above.

Typically, a dextran according to the invention is characterized in that it has 100% α-1,6 glycosidic bonds, a weight-average molar mass Mw of between 2×10$^3$ and 40×10$^3$ g·mol$^{-1}$, preferably between 6.5×10$^3$ and 32×10$^3$ g·mol$^{-1}$, preferably between 7×10$^3$ and 25×10$^3$ g·mol$^{-1}$, and a polydispersity index Ip of less than 1.5. A specific embodiment relates to such a dextran, able to be obtained by the process in accordance with the invention and as described above.

Thus, the dextrans in accordance with the invention are perfectly linear, in that they have no branching, as can be demonstrated with a method for measuring by proton NMR with the Bruker Advance (500 MHz) spectrometer (cf. Experimental results). Moreover, the dextrans in accordance with the invention typically have a medium molar mass (2×10$^3$ to 40×10$^3$ g·mol$^{-1}$, preferably between 6.5×10$^3$ and 32×10$^3$ g·mol$^{-1}$, preferably between 7×10$^3$ to 25×10$^3$ g·mol$^{-1}$), determined by HPSEC, and are barely polydisperse. This result is very surprising when it is obtained by a dextransucrase according to the invention, since the glucansucrases of the GH-70 family are known to generally synthesize α-glucans of very high molar masses, from 10$^6$ to 10$^8$ Da (7-11).

A specific embodiment of the invention also relates to a dextransucrase which has been immobilized.

A subject of the invention therefore relates to a complex comprising a support and a protein with dextransucrase activity according to the invention, characterized in that said protein with dextransucrase activity has been immobilized on said support.

Hereinafter, said complex obtained will sometimes be referred to as "immobilized protein with dextransucrase activity" or "immobilized dextransucrase".

As mentioned above, a dextransucrase according to the invention may be immobilized on the support by techniques known to those skilled in the art, for example by the formation of ionic and/or hydrophobic bonds between the support and the protein (adsorption), formation of covalent bonds between the support and the protein, inclusion of the protein in the support or encapsulation of the protein in the support. A dextransucrase according to the invention which has been immobilized on a support has several advantages, including those of increasing the stability of said immobilized dextransucrase with regard to temperature, pH, etc., of enabling the reuse of said dextransucrase over several successive syntheses, of enabling the development of semi-continuous and/or continuous processes, etc.

Preferably, a method for immobilization by adsorption or by formation of covalent bonds between the support and the protein may be used.

A specific embodiment of the invention therefore relates to a complex as defined above, characterized in that said dextransucrase has been immobilized on said support by formation of covalent, ionic and/or hydrophobic bonds between the support and the protein.

Those skilled in the art will know how to determine the most suitable support depending on the immobilization method used, especially making it possible to obtain good immobilization yields and also high activity of the immobilized enzyme.

For example, it is possible to use, as support for a method for immobilization by adsorption, highly porous polymethacrylate with an amino group as functional group, with short spacer (for example Sprinbeads AA130® sold by Sprin Technologies), polymethacrylate with an octadecyl group as functional group (for example Sprinbeads AO1100 sold by Sprin Technologies), polystyrene—DVB (divinylbenzene) (for example Sprin beads SN110® sold by Sprin Technologies) or epoxy methacrylate with an epoxy group as functional group (for example Purolite ECR8214® sold by Purolite).

It is possible to use, as support for a method for immobilization by ionic bonds between the support and the protein, polymethacrylate with a quaternary amine group as functional group (for example Sepabeads ECQ1A® sold by Resindion) or styrene with a quaternary amine group as functional group (for example Purolite ECR1604® sold by Purolite).

Such an immobilization is preferably carried out with epoxy methacrylate, with an epoxy group as functional group, especially Purolite ECR8214® sold by Purolite.

Particularly advantageously, the molar mass of a dextran synthesized from an immobilized dextransucrase according to the invention may, just like a dextransucrase according to the invention which is not immobilized, be very precisely controlled by the choice of the temperature and the sucrose concentration. This makes it possible to very precisely provide a broader range of dextrans in terms of molar mass, since under identical conditions an immobilized dextransucrase according to the invention advantageously produces dextrans with lower masses than those produced by a dextransucrase according to the invention which is not immobilized (cf. experimental results).

Thus, a specific embodiment of the invention relates to a process for synthesizing dextrans, in which:
sucrose is provided in a synthesis medium,
a complex according to the invention is placed in contact with said sucrose in said synthesis medium, to form dextrans,
the dextrans obtained are optionally isolated.

Another subject of the invention relates to a dextran able to be obtained by said process for synthesizing dextrans.

Preferably, a dextran obtained in this way is characterized in that it has 100% α-1,6 glycosidic bonds, a weight-average molar mass Mw of between $3\times10^3$ and $10\times10^3$ g·mol$^{-1}$, preferably between $4.2\times10^3$ and $7.3\times10^3$ g·mol$^{-1}$, and a polydispersity index Ip of less than 1.5.

Typically, at a temperature fixed at 30° C., a dextransucrase with the amino acid sequence SEQ ID NO: 2 immobilized on a Purolite ECR8214® support produces a dextran with a molar mass of $7\times3\times10^3$ g·mol$^{-1}$ from 50 g·l$^{-1}$ of sucrose and a dextran with an average molar mass of $4.2\times10^3$ g·mol$^{-1}$ from 450 g·L$^{-1}$ of sucrose.

The invention also relates to the synthesis of glucooligosaccharides. Glucooligosaccharides are oligosaccharides consisting of a chain of glucosyl units attached via glycosidic bonds (for example α-1,6, α-1,2, α-1,3 and/or α-1,4). The acceptor reactions carried out consist of a transfer of glucosyl residues from sucrose to other carbohydrate acceptor molecules added to the synthesis medium.

A subject of the invention thus relates to a process for synthesizing glucooligosaccharides, in which:
sucrose and at least one carbohydrate acceptor are provided in a synthesis medium,
a dextransucrase or a complex according to the invention is placed in contact with said sucrose and said at least one carbohydrate acceptor in said synthesis medium, to form glucooligosaccharides,
the glucooligosaccharides obtained are optionally isolated.

Those skilled in the art know which carbohydrate acceptor to use as a function of the type of glucooligosaccharide they wish to obtain.

For example, said at least one carbohydrate acceptor is chosen from glucose, maltose, isomaltose, maltooligosaccharides and glucooligosaccharides, and preferably chosen from glucose, maltose and/or isomaltose.

The same synthesis conditions as described above (synthesis medium, temperature, pH, initial sucrose concentration, etc.) are applicable to the present process for synthesizing glucooligosaccharides.

Another subject of the invention relates to a glucooligosaccharide able to be obtained by the process for synthesizing glucooligosaccharides described above.

According to a specific embodiment of the invention, the glucooligosaccharides obtained are isomaltooligosaccharides. "Isomaltooligosaccharides" are intended to mean oligomers of glucoses bonded solely by α-1,6 bonds. Such isomaltooligosaccharides may be obtained by a process for synthesizing glucooligosaccharides as defined above, in which said at least one carbohydrate acceptor is for example glucose or isomaltose, preferably glucose.

A glucooligosaccharide according to the invention generally has a molar mass of between $0.4\times10^3$ and $5\times10^3$ g·mol$^{-1}$, preferably between $0.7\times10^3$ and $3.4\times10^3$ g·mol$^{-1}$.

Typically, at a temperature fixed at 30° C., the process for synthesizing glucooligosaccharides according to the invention makes it possible to obtain, from a protein with dextransucrase activity with the amino acid sequence SEQ ID NO: 2, a glucooligosaccharide with an average molar mass of $6.8 \times 10^2$ g·mol$^{-1}$ from 315 g·l$^{-1}$ of glucose and 60 g·l$^{-1}$ of sucrose and a glucooligosaccharide with an average molar mass of $3.4 \times 10^3$ g·mol$^{-1}$ from 88 g·l$^{-1}$ of glucose and 110 g·l$^{-1}$ of sucrose.

Typically, at a temperature fixed at 30° C., the process for synthesizing glucooligosaccharides according to the invention makes it possible to obtain, from a protein with dextransucrase activity with the amino acid sequence SEQ ID NO: 2, immobilized on a Purolite ECR8214® support, a glucooligosaccharide with an average molar mass of $7 \times 10^2$ g·mol$^{-1}$ from 333 g·l$^{-1}$ of glucose and 166 g·l$^{-1}$ of sucrose and a glucooligosaccharide with an average molar mass of $2.4 \times 10^3$ g·mol$^{-1}$ from 88 g·l$^{-1}$ of glucose and 110 g·l$^{-1}$ of sucrose.

The invention also relates to the synthesis of glucoconjugates. Indeed, glucansucrases may be used for the synthesis of glucoconjugates by acceptor reaction, by introducing, in addition to the sucrose, a hydroxylated molecule into the synthesis medium.

The glucosylation of hydroxylated molecules may be advantageous for the synthesis of novel compounds, or for a modification of physicochemical properties, such as solubility, for example.

"Hydroxylated molecule" is intended to mean any non-carbohydrate molecule containing at least one free hydroxyl group. Typically, a hydroxylated molecule is a flavonoid, polyol or amino acid. It is possible for example to glycosylate catechols, polyphenols or alkyl polyglucosides.

A subject of the invention thus relates to a process for synthesizing glucoconjugates, in which:
- sucrose and at least one hydroxylated molecule are provided in a synthesis medium,
- a dextransucrase or a complex according to the invention is placed in contact with said sucrose and said at least one hydroxylated molecule in said synthesis medium, to form glucoconjugate compounds.
- the glucoconjugate compounds obtained are optionally isolated.

The same synthesis conditions as described above (synthesis medium, temperature, pH, initial sucrose concentration, etc.) are applicable to the present process for synthesizing glucoconjugates.

Another subject of the invention relates to a glucoconjugate able to be obtained by the process for synthesizing glucoconjugates described above.

Products according to the invention, especially dextrans, glucooligosaccharides or glucoconjugates in accordance with the invention, may be used in any type of application for which their functional characteristics, especially their size and their type of glycosidic bonds, are suitable.

A dextran, glucooligosaccharide or glucoconjugate according to the invention may for example be used in pharmaceutical, cosmetic or food-grade applications. For the possible applications, reference may be made to the publication by Vettori et al. (12). By way of nonlimiting illustration, a dextran according to the invention may be used as support or base (for example in a vaccine or in a pharmaceutical composition) (13), as neutraceutical agent (13, 14), as stabilizer (for example stabilizer for an antigen in a vaccine, or stabilizer for proteins or lyophilized products), as immunostimulant or prebiotic (15), as agent for preventing the crystallization of sugars, as blood plasma substitute, as iron transporter in the treatment of serious anaemias (14), as anticoagulant, as blood plasma extender, in the prevention of postoperative shock, in the treatment of burns, and in the reduction of the risks of thrombosis or embolisms, as active agent or excipient in ophthalmic solutions, as excipient during lyophilization as diluent and/or collapse temperature modifier, as cryoprotectant or as organ storage agent for transplant.

One subject of the invention relates to a pharmaceutical, cosmetic or food-grade composition comprising a dextran according to the invention, a glucooligosaccharide according to the invention or a glucoconjugate according to the invention as active agent or as acceptable excipient.

Finally, the invention relates to derivatives of dextrans of the invention. The term "dextran derivative" is intended here to mean a dextran of the invention which undergoes one or more known chemical modification steps, especially chosen from etherification, esterification or crosslinking. It is thus possible to obtain a dextran derivative such as a crosslinked dextran, a dextran ester, for example an inorganic dextran ester (dextran phosphate, dextran sulfate) or an organic dextran ester, a dextran ether, for example a nonionic dextran ether (alkylated dextran, dextrin hydroxyalkyl ether or hydroxyalkylaryl ether, poly(ethylene glycol) alkyl dextran ether) or an ionic dextran ether (sulfopropylated dextran, carboxymethylated dextran, 2 (diethylamino)ethyl dextran). Such chemical modification techniques and also the applications for which the dextrans thus obtained are suitable, are well known to those skilled in the art. Reference may for example be made to the document Heinze et al. (16) and to the thesis by Ndegwa Henry Maina (17).

One subject of the invention thus relates to a process for modifying a dextran in accordance with the invention, in which the dextran undergoes one or more chemical modification steps.

Advantageously, a chemical modification step is chosen from etherification, esterification and crosslinking.

FIGURES

FIG. 1: Diagrammatic representation of the primary structure of DsrM (based on the protein alignment with the GFT180 enzyme from *Lactobacillus reuteri* 180). Five domains are distinct: domain V in white, domain IV in light gray, domain B striped, domain A "bubbled" and domain C in black. The repeat motifs YG according to the definition of Giffard and Jacques are represented by a checkered pattern.

FIG. 2: Diagrammatic representation of the primary structures of DsrM, DsrM ΔPS ΔC-APY and DsrM Δ174-1317. Five domains are distinct: domain V in white, domain IV in light gray, domain B striped, domain A "bubbled" and domain C in black. The repeat motifs YG according to the definition of Giffard and Jacques are represented by a checkered pattern.

FIG. 3: Characteristics of the commercially available immobilization supports used for immobilization of the enzyme DsrM ΔPS ΔC-APY.

Figure 4:
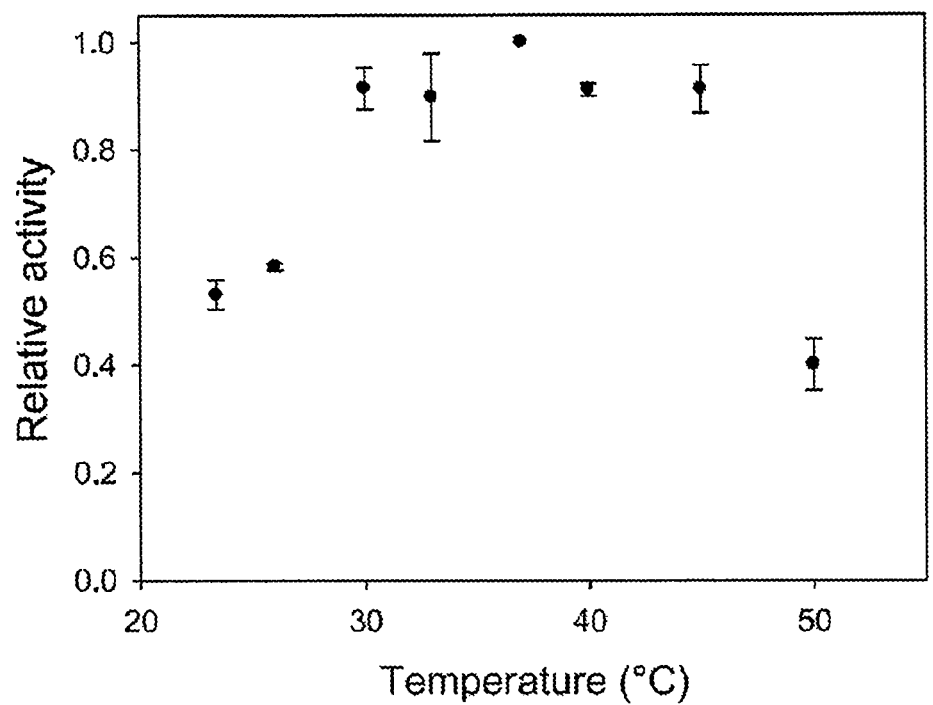

FIG. 4: Graphic representation of the enzymatic activity of the truncated dextransucrase DsrM ΔPS ΔC-APY as a function of temperature under standard conditions, starting from 100 g·l$^{-1}$ of sucrose in 50 mM of sodium acetate, pH 5.75.

Figure 5:
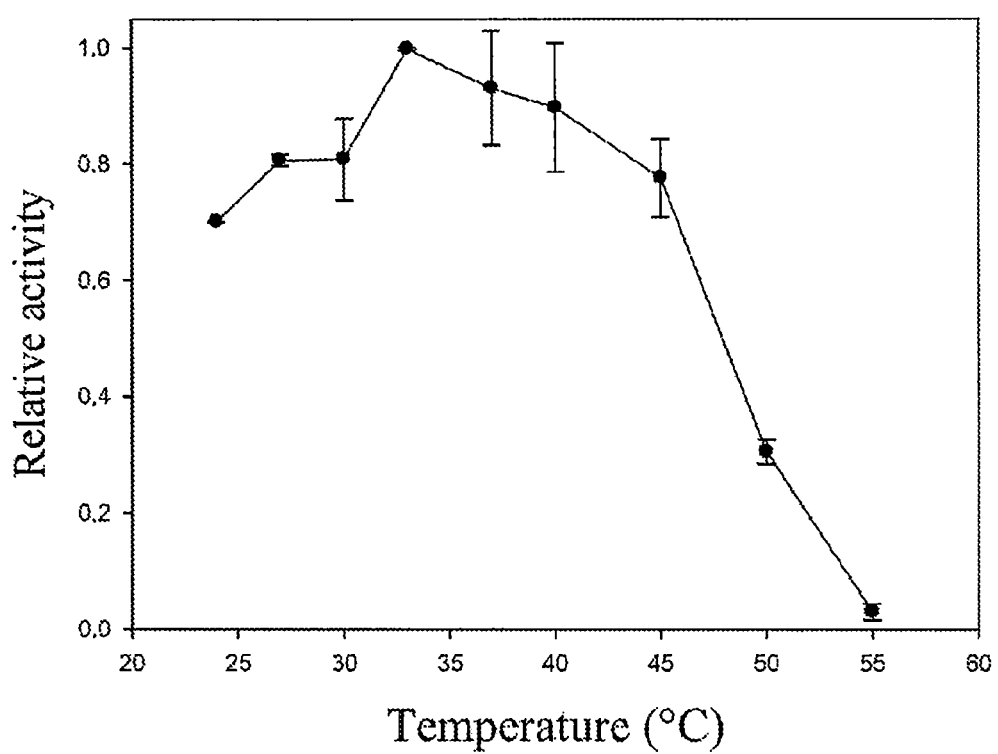

FIG. 5: Graphic representation of the enzymatic activity of the whole dextransucrase DsrM as a function of temperature under standard conditions, starting from 100 g·l$^{-1}$ of sucrose in 50 mM of sodium acetate, pH 5.75.

Figure 6:
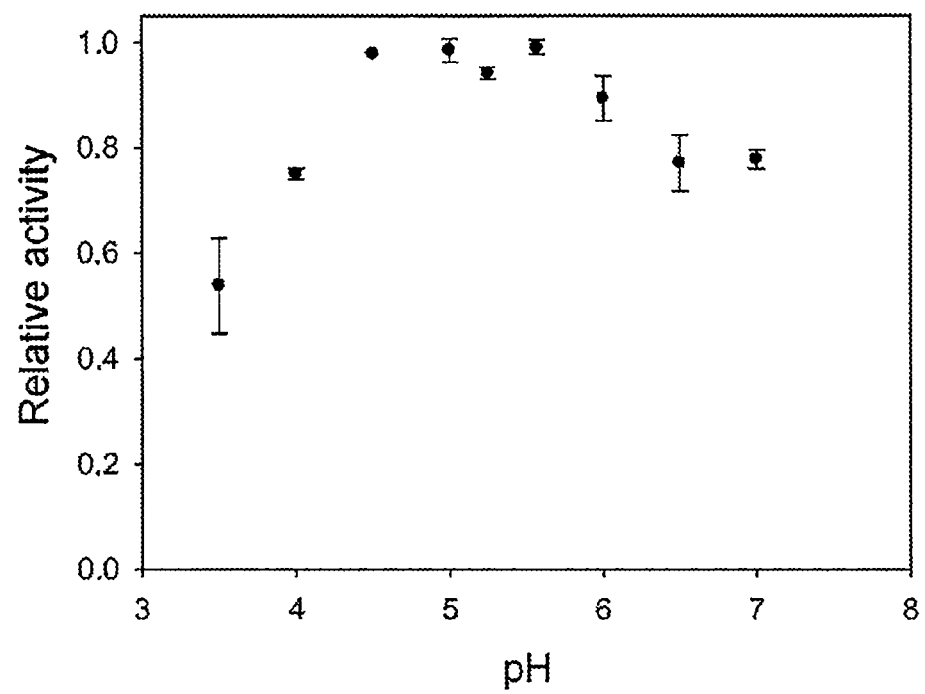

FIG. 6: Graphic representation of the enzymatic activity of the truncated dextransucrase DsrM ΔPS ΔC-APY as a function of pH under standard conditions, starting from 100 g·l$^{-1}$ of sucrose at 30° C.

Figure 7:
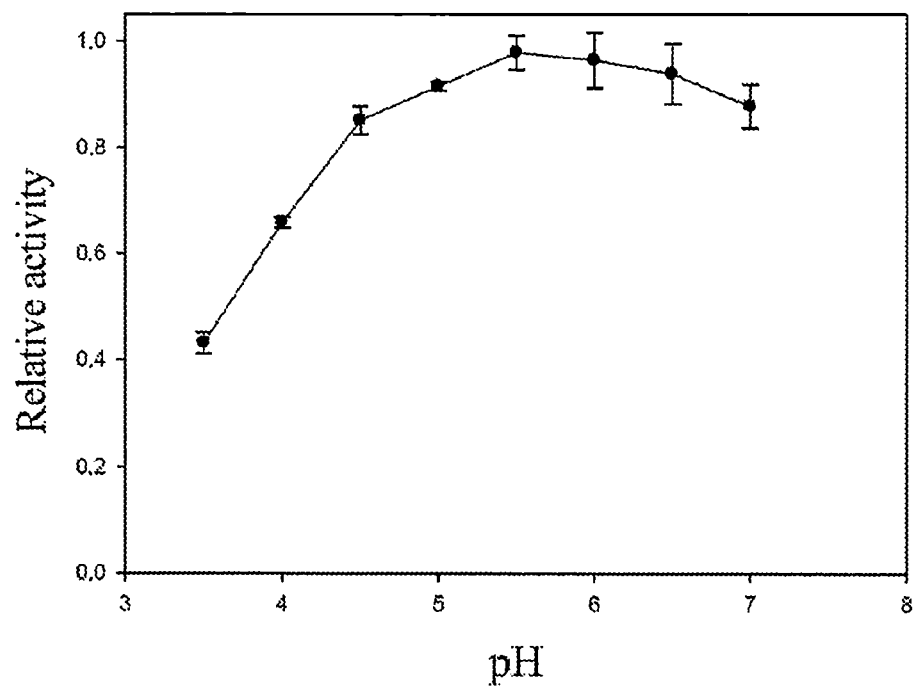

FIG. 7: Graphic representation of the enzymatic activity of the whole dextransucrase DsrM as a function of pH under standard conditions, starting from 100 g·l$^{-1}$ of sucrose at 30° C.

Figure 8:
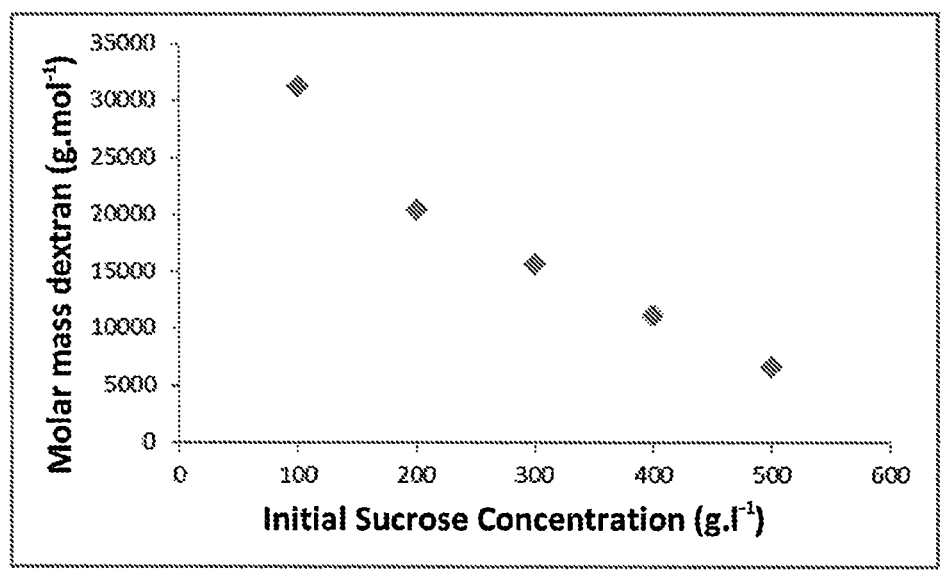

FIG. 8: Representation of the molar mass of the dextrans synthesized by DsrM at 25° C., pH 5.75, as a function of the initial sucrose concentration.

Figure 9:
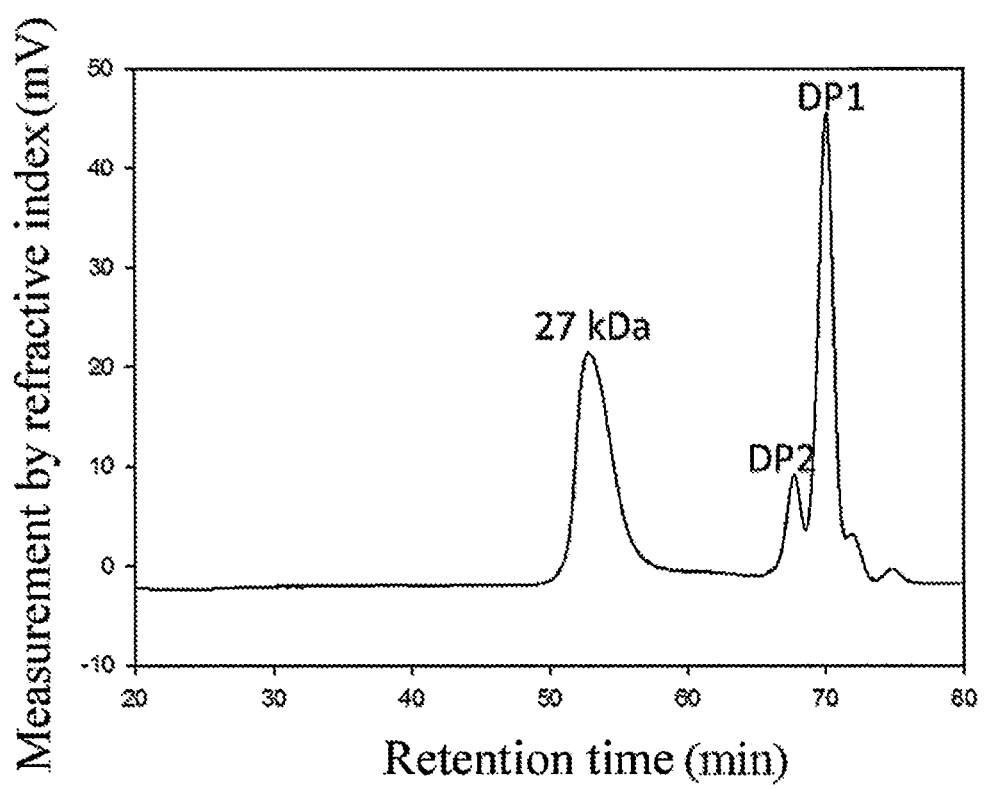
Figure 10A:
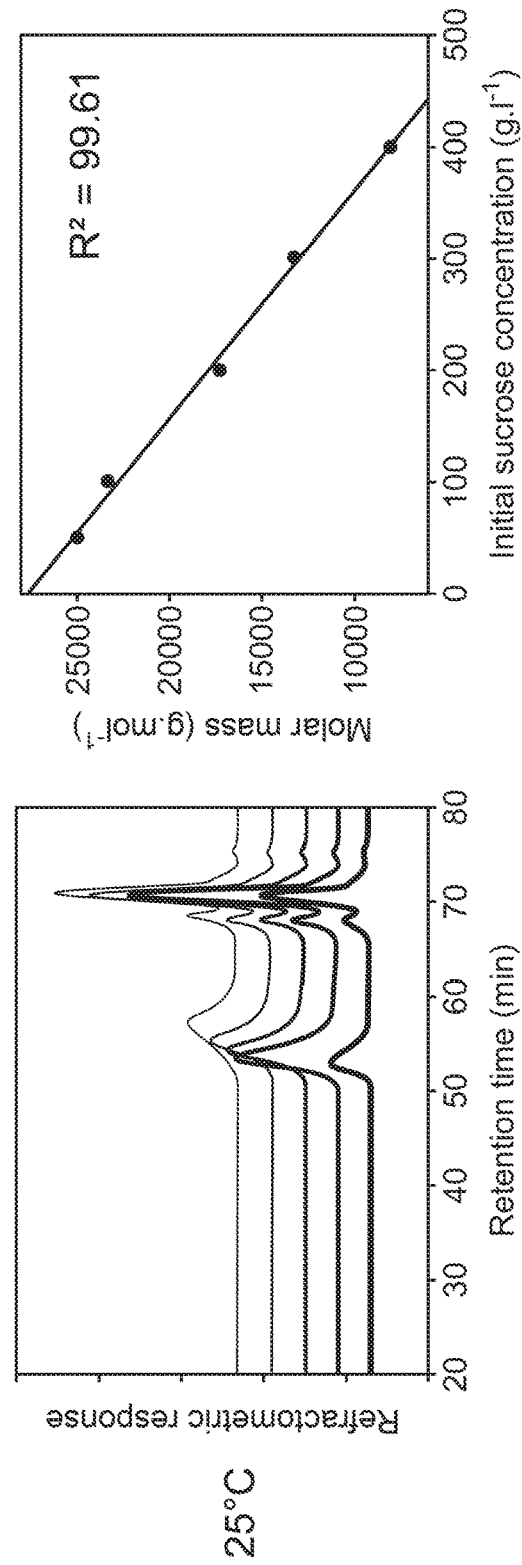
Figure 10B:
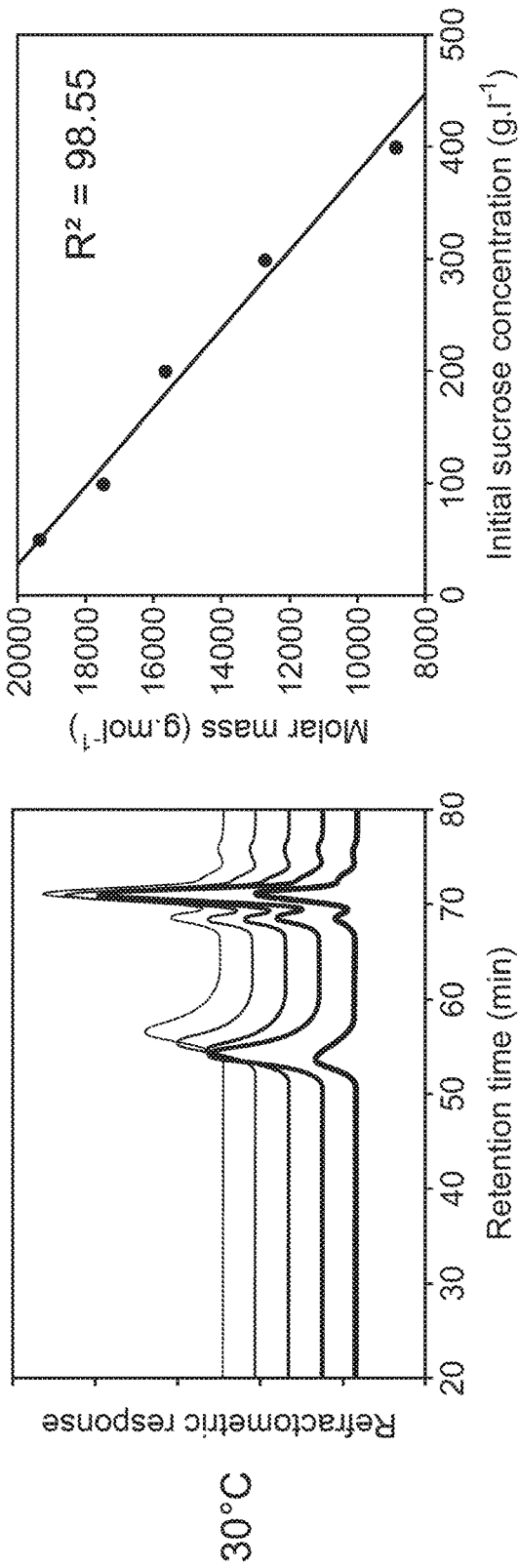
Figure 10C:
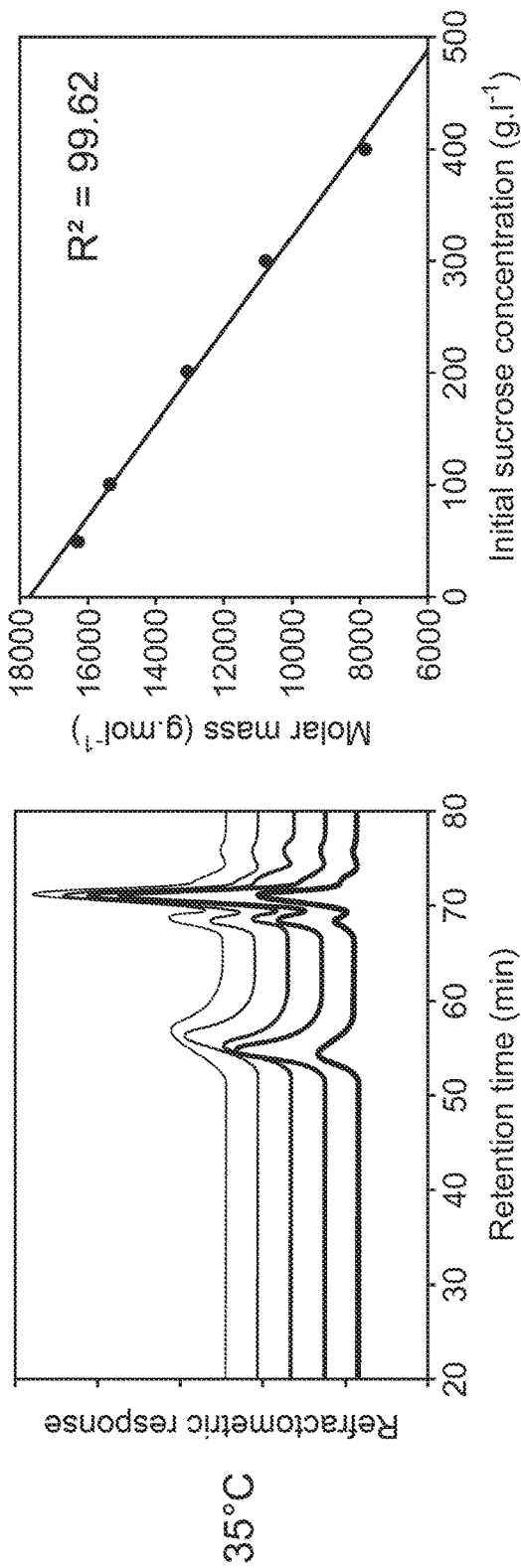
Figure 10D:
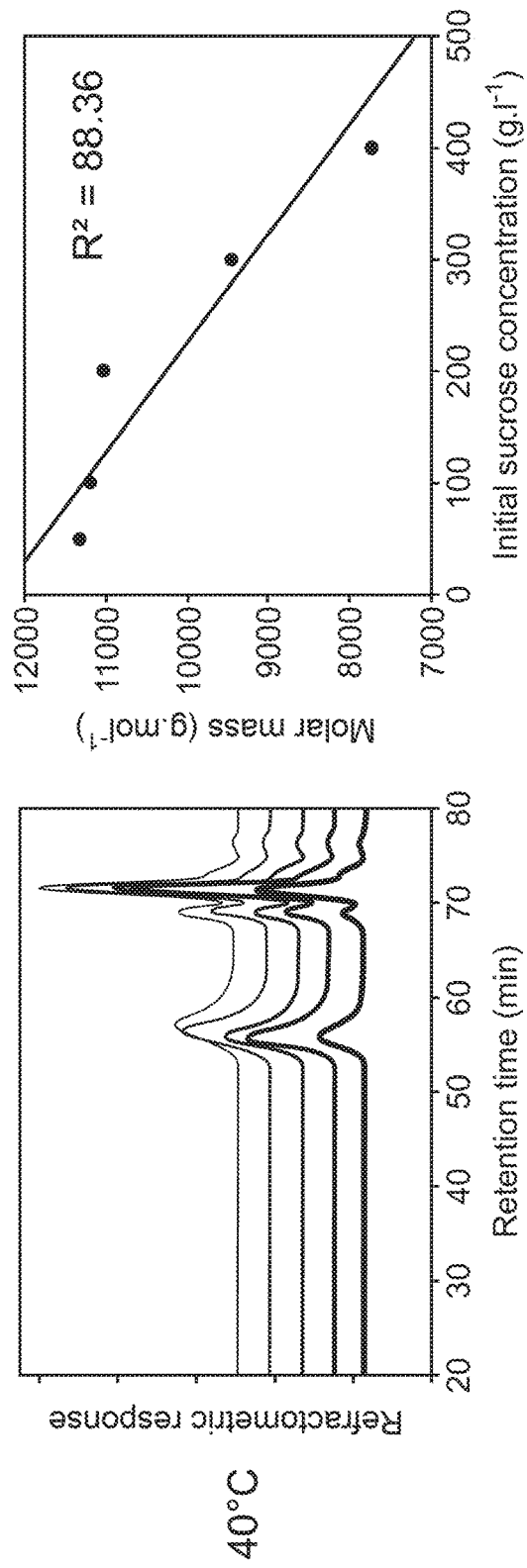
Figure 11A:
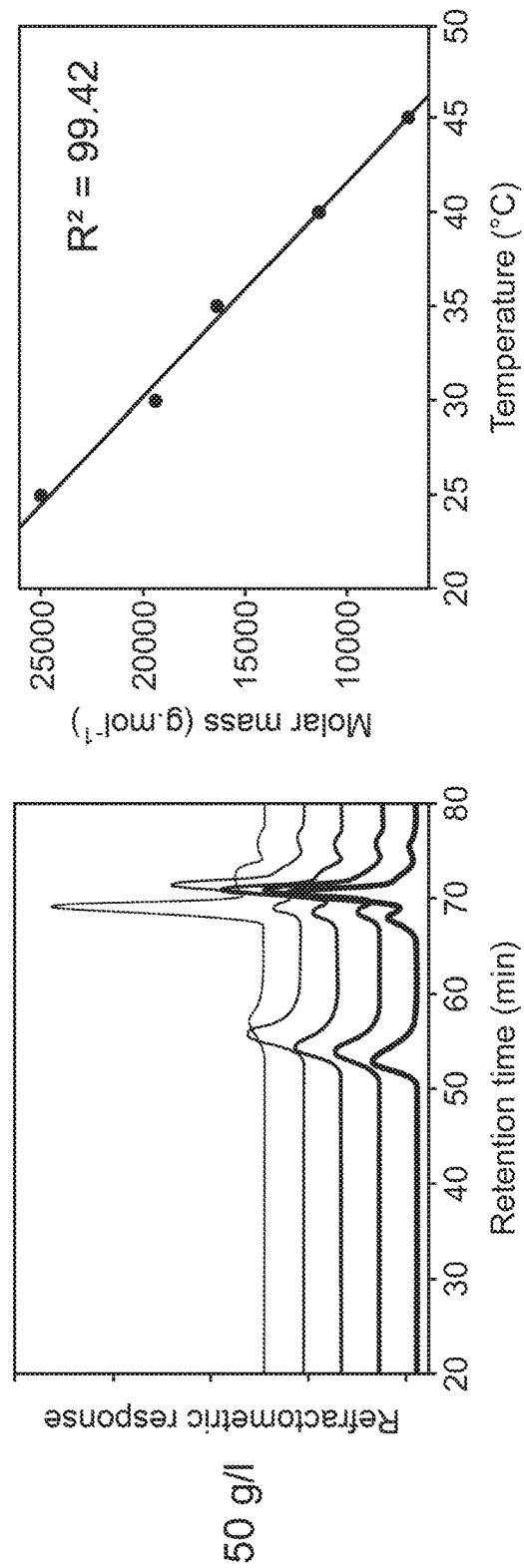
Figure 11B:
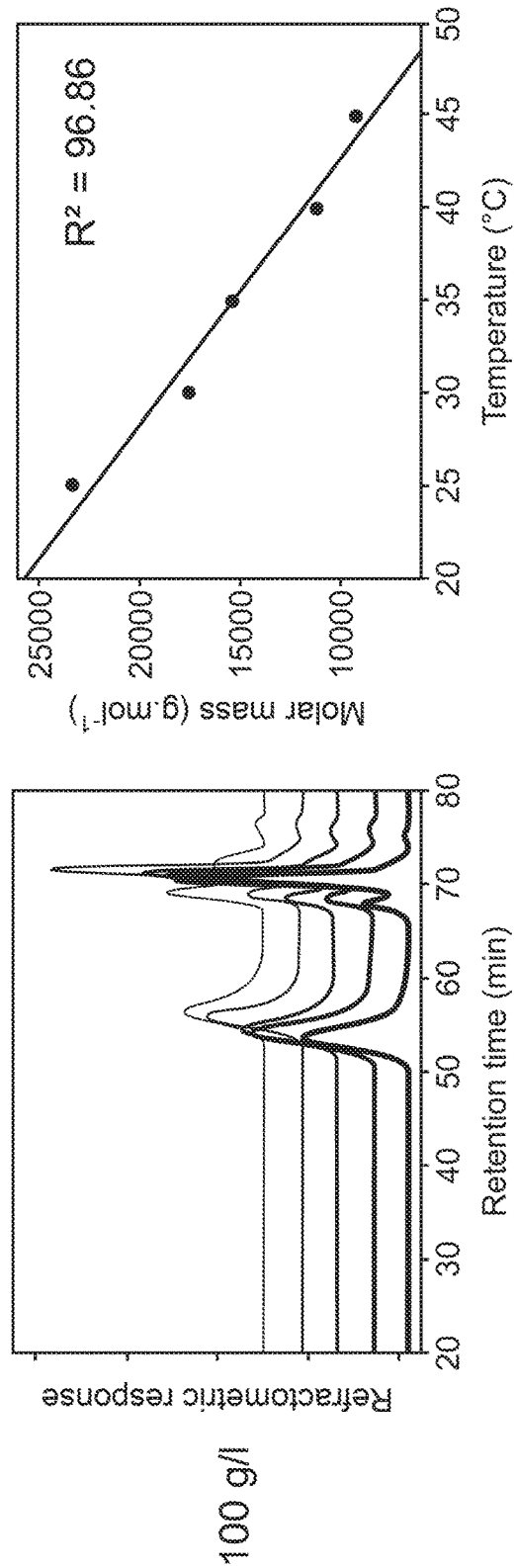
Figure 11C:
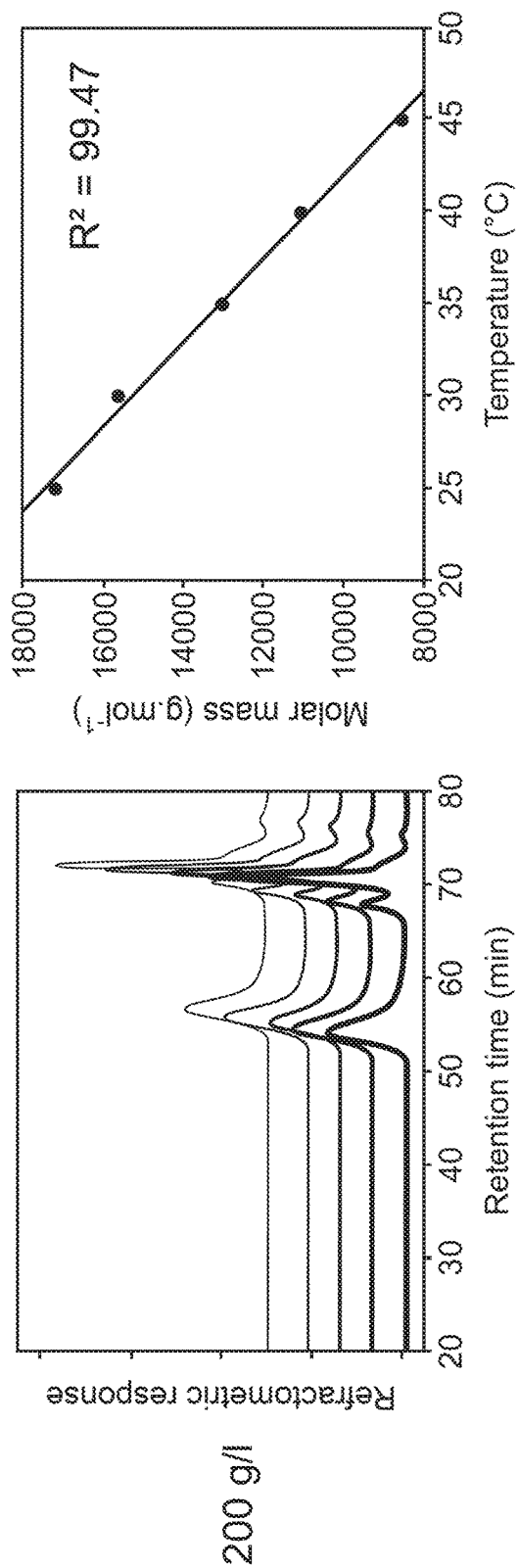
Figure 11D:
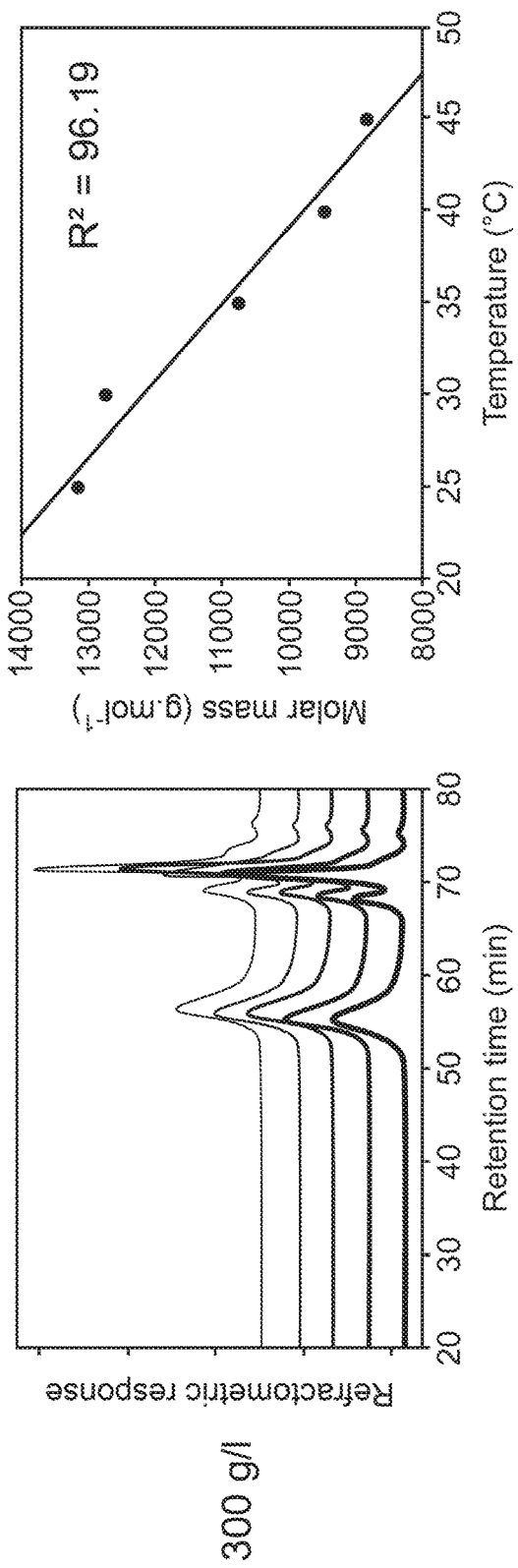
Figure 11E:
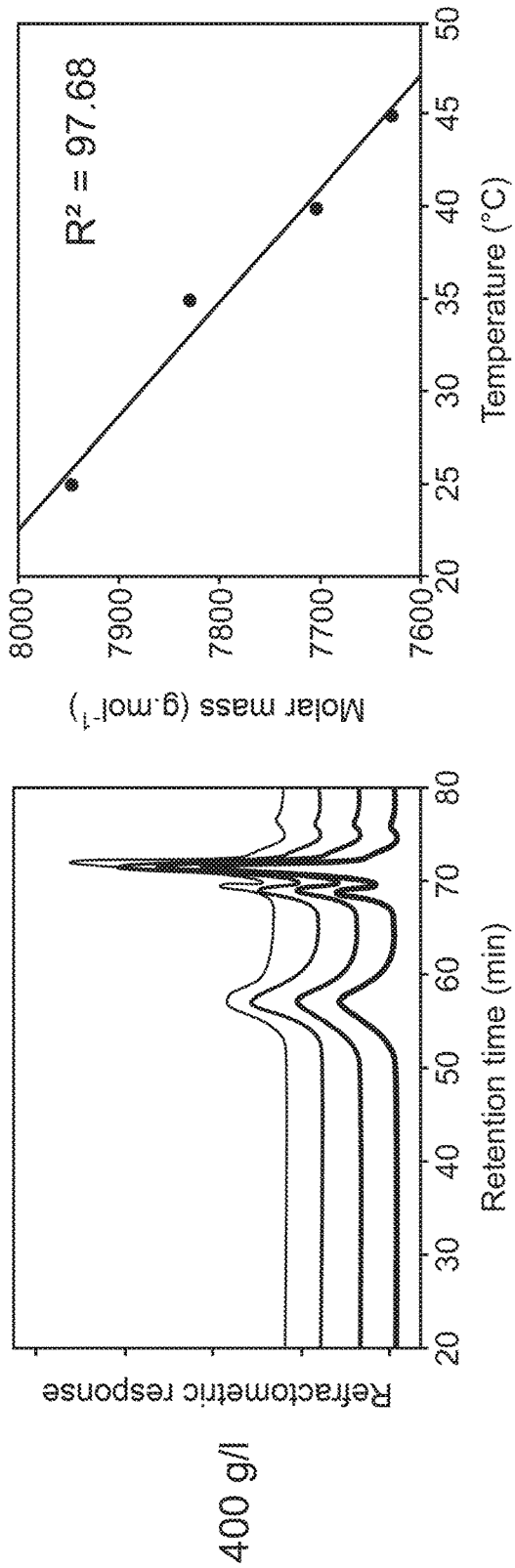

FIG. 9: HPSEC-RI profile of the products synthesized by DsrM (whole form), after 24 h of reaction starting from 100 g·l$^{-1}$ of sucrose at 30° C., pH 5.75.

FIG. 10: Right-hand graphs: Control of the molecular mass of the dextrans synthesized by the enzyme DsrM ΔPS ΔC-APY at fixed temperature: 25° C. (A), 30° C. (B), 35° C. (C), 40° C. (D), varying the initial substrate (sucrose) concentration.

Left-hand graphs: HPSEC-RI profiles of the enzymatic reactions at t=24 h starting from 50 g·l$^{-1}$, 100 g·l$^{-1}$, 200 g·l$^{-1}$, 300 g·l$^{-1}$ and 400 g·l$^{-1}$ of sucrose (curves going from the bottom to the top, respectively) with fixed temperature: 25° C. (A), 30° C. (B), 35° C. (C), 40° C. (D).

FIG. 11: Right-hand graphs: Control of the molecular mass of the dextrans synthesized by the enzyme DsrM ΔPS ΔC-APY at fixed initial sucrose concentration: 50 g·l$^{-1}$ (A), 100 g·l$^{-1}$ (B), 200 g·l$^{-1}$ (C), 300 g·l$^{-1}$ (D) and 400 g·l$^{-1}$ (E), varying the temperature.

Left-hand graphs: HPSEC-RI profiles of the enzymatic reactions at t=24 h at 25° C., 30° C., 35° C., 40° C. and 45° C. (curves going from the bottom to the top, respectively) with fixed initial sucrose concentration: 50 g·l$^{-1}$ (A), 100 g·l$^{-1}$ (B), 200 g·l$^{-1}$ (C), 300 g·l$^{-1}$ (D) and 400 g·l$^{-1}$ (E).

Figure 12:
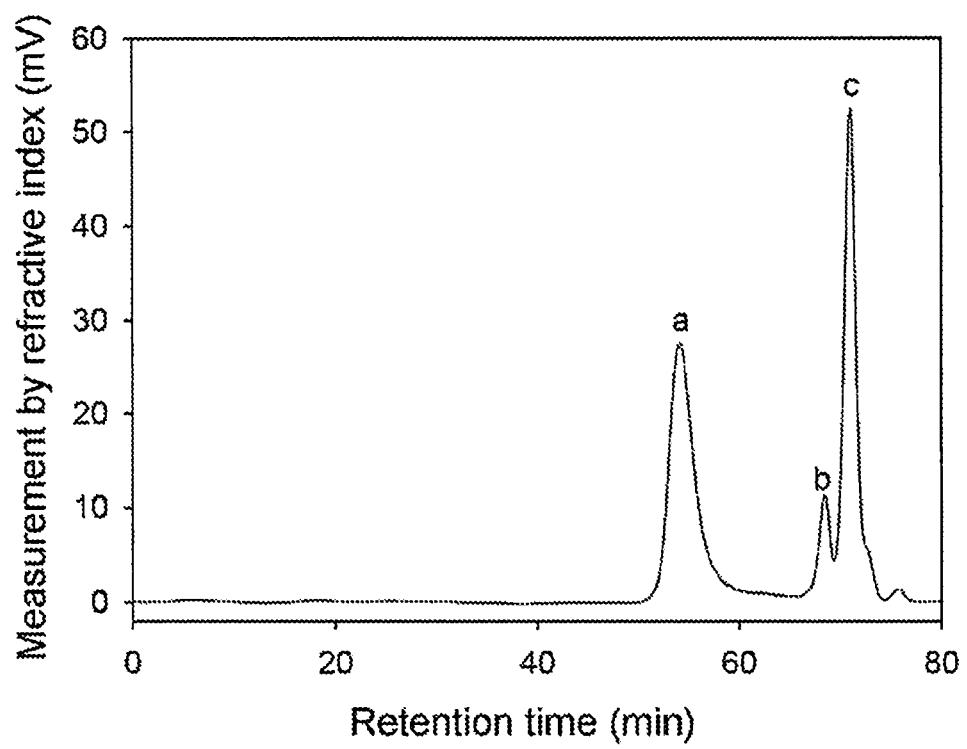

FIG. 12: HPSEC-RI profile of the dextrans synthesized by DsrM ΔPS ΔC-APY at the end of the reaction starting from 100 g·l$^{-1}$ of sucrose at 30° C., pH 5.75, with a: polymer of average molecular weight of 17.5 kDa, b: disaccharides (leucrose present in the final synthesis mix) and c: monosaccharides (fructose and glucose).

Figure 13:
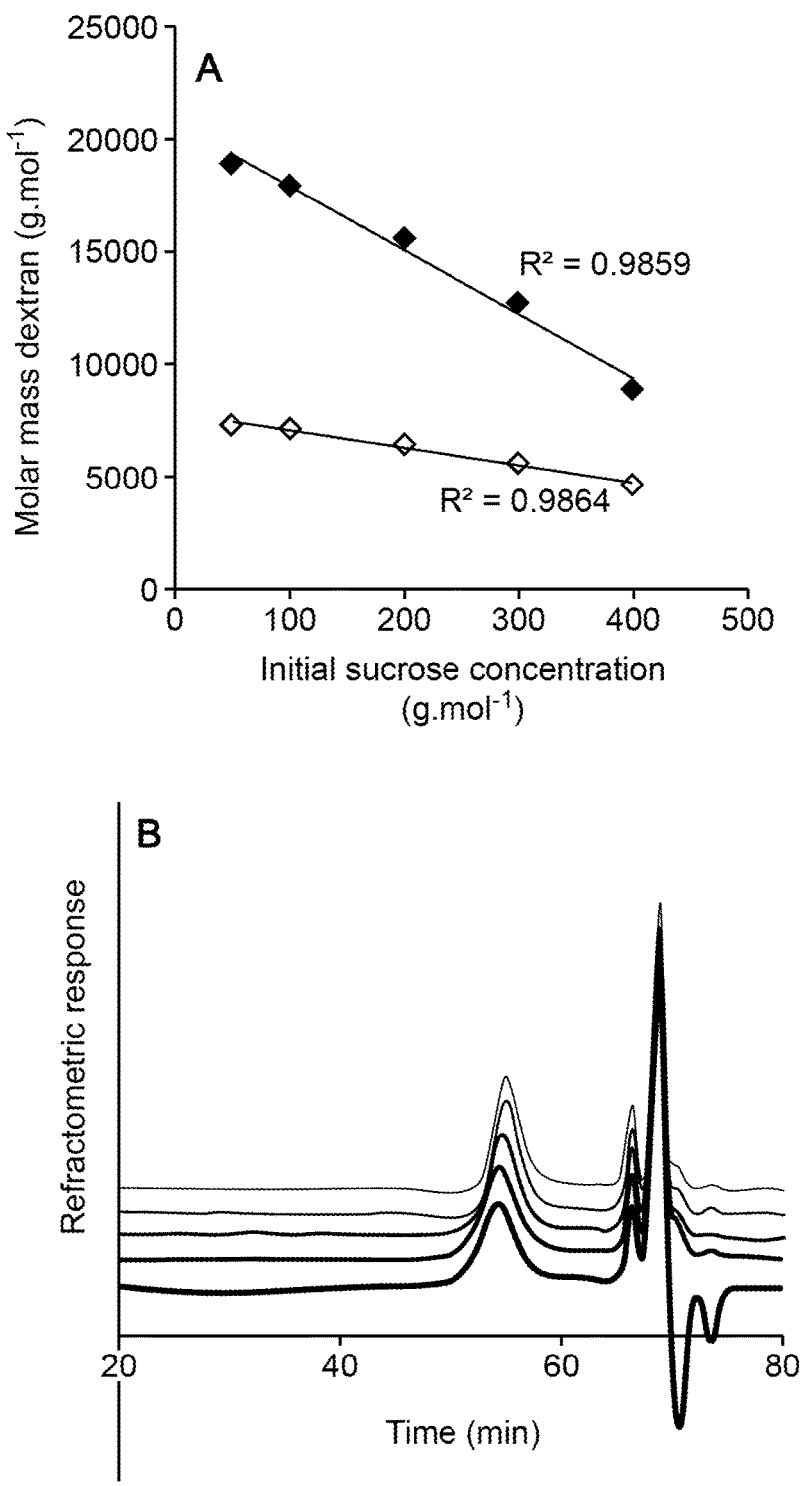

FIG. 13: A: Comparison of the average molar mass of the dextrans synthesized by the enzyme DsrM ΔPS ΔC-APY when free (black marker) and when immobilized on a Purolite ECR8214® support (white marker) at 30° C. and as a function of increasing initial sucrose concentrations (50 g·l$^{-1}$, 100 g·l$^{-1}$, 200 g·l$^{-1}$, 300 g·l$^{-1}$ and 400 g·l$^{-1}$)

B: HPSEC-RI profiles of the enzymatic reactions catalyzed by immobilized DsrM ΔPS ΔC-APY at t=24 h starting from 50 g·l–1, 100 g·l–1, 200 g·l$^{-1}$, 300 g·l$^{-1}$ and 400 g·l$^{-1}$ of sucrose (curves going from the bottom to the top, respectively).

Figure 14:
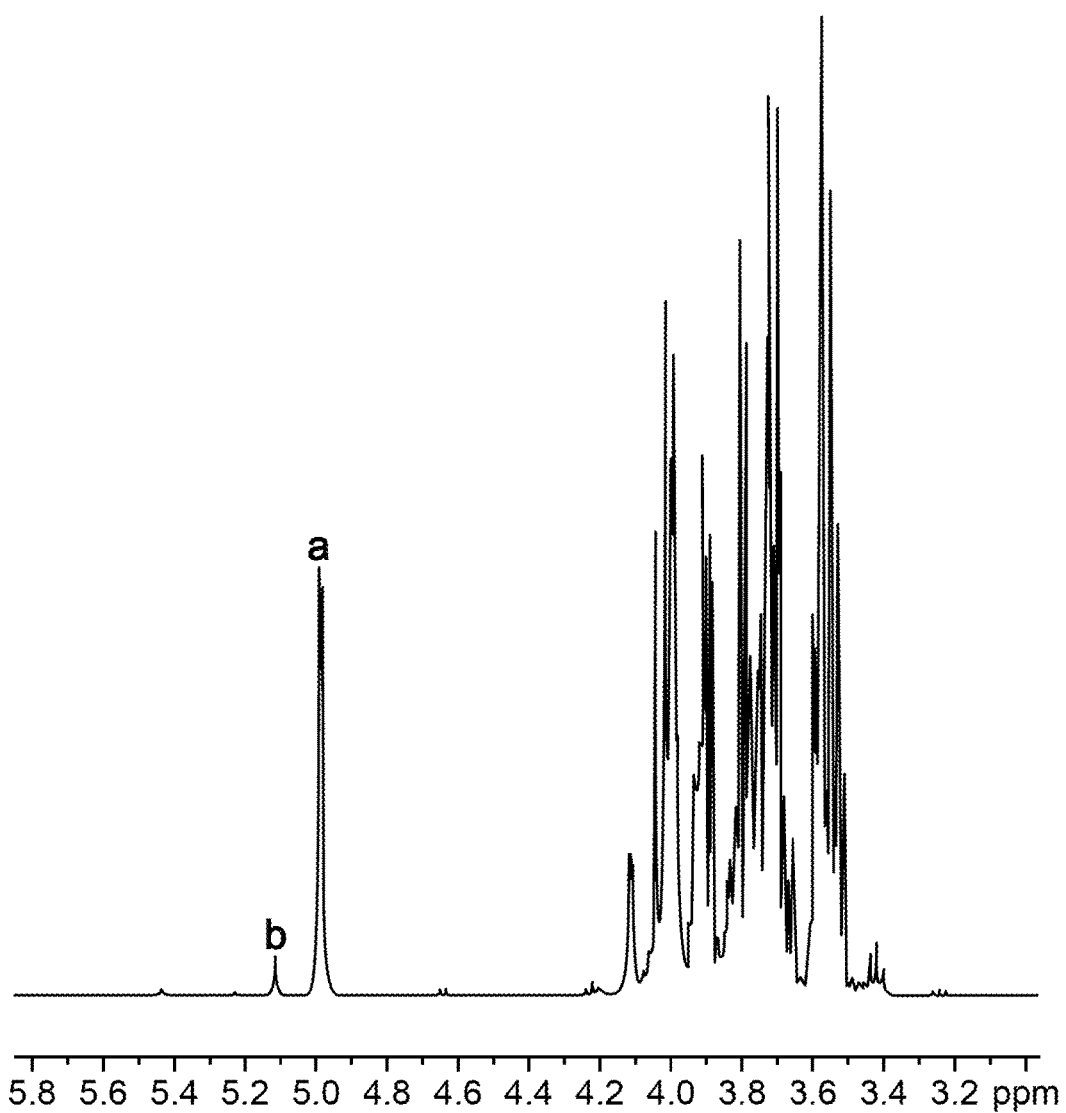

FIG. 14: $^1$H NMR spectrum of the products synthesized by DsrM after 24 h of reaction starting from 100 g·l$^{-1}$ of sucrose at 30° C., pH 5.75 with a) α-1,6 bonds, b) leucrose.

Figure 15:
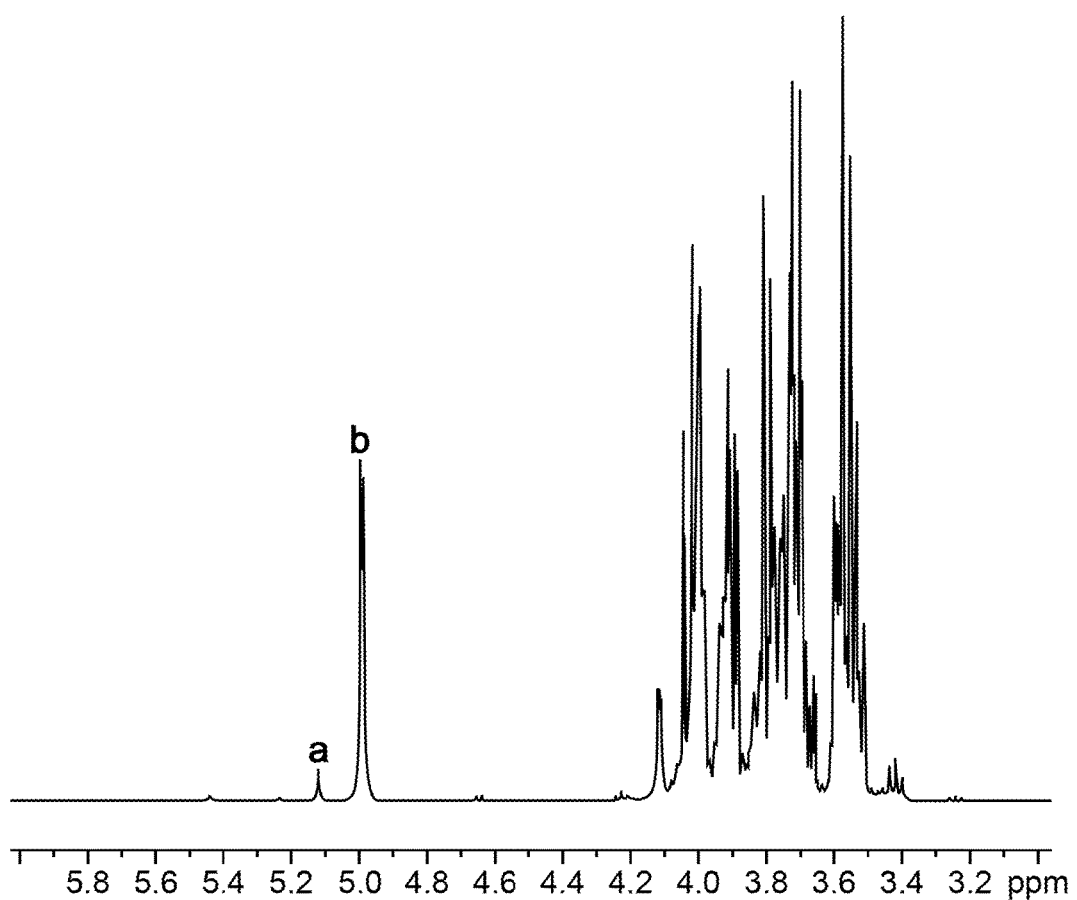

FIG. 15: $^1$H NMR spectrum of the products synthesized by DsrM ΔPS ΔC-APY at the end of the reaction starting from 100 g·l$^{-1}$ of sucrose at 30° C., pH 5.75 with a) leucrose, b) α-1,6 bonds.

EXAMPLES

Example 1: Identification of the dsrm Gene in the *Leuconostoc citreum* NRRL B-1299 Genome and Analysis of the Primary Structure of the Corresponding Protein The dsrm gene was identified in the genome of *Leuconostoc citreum* NRRL B-1299 by nucleotide blast against a database consisting of glucansucrase nucleotide sequences listed in glycoside hydrolase family 70 according to CAZY classification (Carbohydrate Active enZYme database, www.cazy.org/GH70_all.html).

The gene was translated into protein sequence using the Transeq software from EMBOSS (www.ebi.ac.uk/Tools/st/emboss_transeq/).

A sequence encoding a signal peptide was identified by the SignalP server 4.1 software (www.cbs.dtu.dk/services/SignalP/).

Multiple protein alignments (with the overall alignment software ClustalW2, available online, www.ebi.ac.uk/Tools/msa/clustalw2/) with other characterized glucansucrases made it possible to identify the conserved motifs of the catalytic core of DsrM, and to cut the enzyme up into various protein domains (A, B, C, IV and V).

The various identity and similarity percentages between protein sequences, indicated in the preliminary sheet for the invention, were calculated with the BlastP tool (protein-protein Blast) from the NCBI, available online (blast.ncbi.nlm.nih.gov/Blast.cgi?PROGRAM=blastp&PAGE_TYPE=BlastSearch&LINK_L OC=blasthome) and using the default parameters proposed by the site.

Example 2: Cloning the dsrm Gene

The dsrm gene was amplified by PCR from the genomic DNA of *Leuconostoc citreum* NRRL B-1299 and using the two primers presented in table 1.

TABLE 1

| Primer | Sequence (5' to 3') |
| --- | --- |
| Forward primer | CACCATGAAAATAAAAGAAACAATTACCCGAAA (SEQ ID NO: 3) |
| Reverse primer | AAGCTTGCAAAGCACGCTTATCAATC (SEQ ID NO: 4) |

The addition of the 4 bases, CACC, in the 5' position of the forward primer (underlined in table 1) allowed the correct insertion of the PCR fragment into the entry vector pENTR/D/TOPO (Life Technologies), in order to subsequently perform a cloning using the Gateway technology. A positive entry clone (entry vector containing the PCR fragment in the desired sense) was selected and recombined with the destination vector pET-53-DEST (Novagen) using the LR clonase enzyme mix II (Life Technologies). The positive recombinant clones were selected and analyzed by restriction. The absence of mutation in the plasmids was confirmed by sequencing (GATC).

Example 3: Cloning of the dsrm Δps Δc-apy Gene

The dsrm Δps Δc-apy gene was amplified by PCR from the plasmid pET-55/DsrM previously constructed in example 2, and using the two primers presented in table 2.

TABLE 2

| Primer | Sequence (5' to 3') |
| --- | --- |
| Forward primer | CACCCAAACGCCGGTTGGTACAACACAG (SEQ ID NO: 5) |
| Reverse primer | TTTTGCCATCGTACCATCGTTATT (SEQ ID NO: 6) |

The addition of the 4 bases, CACC, in the 5' position of the forward primer (underlined in table 2) allowed the correct insertion of the PCR fragment into the entry vector pENTR/D/TOPO (Life Technologies), in order to subsequently perform a cloning using the Gateway technology. A positive entry clone (entry vector containing the PCR fragment in the desired sense) was selected and recombined with the destination vector pET-53-DEST (Novagen) using the LR clonase enzyme mix II (Life Technologies). The positive recombinant clones were selected and analyzed by restriction. The absence of mutation in the plasmids was confirmed by sequencing (GATC).

Example 4: Heterologous Expression of dsrm and dsrm Δps Δc-apy in *Escherichia coli*

For the production of the recombinant enzymes, *Escherichia coli* BL21 star DE3 cells were transformed with the corresponding (pET-55/dsrm or pET-55/dsrm Δps Δc-apy) plasmid constructed according to examples 2 and 3. 300 µl of the transformation mix were inoculated into 30 ml of LB (Lysogeny Broth) medium, supplemented with 100 µg·ml$^{-1}$ of ampicillin, and incubated overnight at 37° C. in order to prepare a preculture.

Cultures of 1l in modified ZYM5052 medium (1% glycerol, 0% glucose, 1% lactose, Studier, 2005) were thus inoculated at an initial $OD_{600\,nm}$ of 0.05 using the preculture from the day before, then incubated for 26 hours at 21° C. and 150 rpm. At the end of fermentation, the culture media are centrifuged (15 min, 6500 rpm, 4° C.) and the pellets are concentrated to an OD of 80 in 50 mM of sodium acetate buffer, pH 5.75.

In order to obtain the recombinant enzyme (produced intracellularly by *Escherichia coli*), the cells are ruptured with ultrasound according to the following protocol: 5 cycles of 20 seconds at 30% of the maximum power of the probe, under cold conditions, with 4 minutes of rest in ice between each cycle. The sonication supernatant (containing the soluble recombinant enzyme) is then recovered after 30 minutes of centrifugation (10 000 rpm, 10° C.) and stored at 4° C.

Example 5: Method of Determining the Enzymatic Activity by the DNS Method

One glucansucrase enzymatic unit represents the amount of enzyme which releases one µmol of fructose per minute, at 30° C., from 100 g·l$^{-1}$ of sucrose in 50 mM of sodium acetate, at pH 5.75.

The activity is determined by measuring the initial rate of production of the reducing sugars using the dinitrosalicylic acid (DNS) method. During a time course, 100 µl of reaction medium are removed and the reaction is stopped by adding an equivalent volume of DNS. The samples are then heated for 5 min at 95° C., cooled in ice, and diluted 50/50 in water, and the absorbance is read at 540 nm. A standard range from 0 to 2 g·l$^{-1}$ of fructose makes it possible to establish the link between the absorbance value and concentration of reducing sugars.

Example 6: Immobilization of the Truncated Dextransucrase DsrM ΔPS ΔC-APY

Immobilization was carried out by reacting weights varying between 0.1 g and 0.6 g of different commercial supports with 2.5 ml of sonication supernatant containing the recombinant enzyme DsrM ΔPS ΔC-APY. The pH of this enzymatic solution is controlled and must be between 5.75 and 7.5. The reaction is conducted at 4° C. with gentle agitation (100 rpm). The immobilization is stopped after 16 hours of reaction by filtration and washing with three successive volumes (10 ml) of sodium acetate buffer, pH 5.75, at 50 mM. The immobilized enzyme is stored at 4° C. before use.

The characteristics of the supports tested are given in FIG. 3.

Hereinafter, such an immobilized enzyme is referred to as "immobilized DsrM ΔPS ΔC-APY".

The different immobilization supports were tested for their ability to fix the enzyme DsrM ΔPS ΔC-APY. The screening consisted in placing 250 mg weights of each support in contact with 2.5 ml of sonication supernatant (free initial activity: 16.5 U/ml).

The fixed activity following reaction and washing on the different supports was measured on aliquots of controlled weight from each enzyme batch produced. The reaction volume was also adapted to the activity of each batch, with larger volumes enabling the measurement of the most active enzymes. The results of the screening are given in table 3 below.

TABLE 3

| Support | Weight of enzyme immobilized in reaction (mg) | Reaction volume (ml) | Production of reducing sugars (µmol/min/reaction) | Activity (U/g) |
|---|---|---|---|---|
| Purolite ECR8214 ® | 39.5 | 3 | 1.03 | 77.94 |
| Sprinbeads AO110 ® | 35.8 | 3 | 0.93 | 77.77 |
| Sepabeads ECQ1A ® | 36.7 | 3 | 0.43 | 35.34 |
| Purolite ECR1604 ® | 44.4 | 3 | 0.46 | 31.19 |
| Purolite ECR4204 ® | 56.5 | 1 | 1.71 | 30.27 |
| Sprinbeads AA130 ® | 54.4 | 1 | 1.32 | 24.26 |
| Sprinbeads SN110 ® | 43.4 | 3 | 0.32 | 21.88 |

The different supports, as a function of the measured activity, may be grouped into two categories:
- the 2 supports, Purolite ECR8214® and Sprinbeads AO110®, which have the best activities, of the order of 78 U/g;
- 5 supports having average but good activities, of between 22 and 35 U/g;

Only the support Purolite ECR8214® was then used in order to optimize the immobilization, especially by optimizing immobilization yields, fixed activities, etc.

The optimization of the immobilization of DsrM ΔPS ΔC-APY on Purolite ECR8214® consisted in varying the weight of support between 100 mg and 600 mg placed in contact with a fixed amount of free enzyme (2.5 ml of sonication supernatant having an initial activity of 45 U/ml).

The calculation of three different yields makes it possible to characterize the immobilization:

The fixation yield $R_{fixation}$, which quantifies the total share of enzyme fixed to the supports $$R_{fixation}(\%) = \left(1 - \frac{\text{Initial free activity}}{\text{Final free activity}}\right) \times 100$$

The immobilization yield $R_{immobilization}$, which quantifies the active enzyme immobilized as a function of the total amount of enzyme used for the immobilization $$R_{immobilization}(\%) = \frac{\text{Immobilized activity}}{\text{Introduced free activity}} \times 100$$

The immobilization efficiency, which quantifies the amount of active enzyme immobilized as a function of the total amount of effectively immobilized enzyme $$\text{Efficiency}(\%) = \frac{\text{Immobilized activity}}{(\text{Initial free activity} - \text{final free activity})} \times 100$$

The results of the immobilization are given in table 4 below.

TABLE 4

| Weight for immobilization (mg) | Immobilized activity U/g | Fixation yield % | Immobilization yield % | Efficiency % |
|---|---|---|---|---|
| 105.5 | 144.3 | 44 | 14 | 31 |
| 248.7 | 147.2 | 58 | 33 | 56 |
| 355.6 | 146.0 | 80 | 46 | 58 |
| 456.7 | 148.2 | 92 | 60 | 66 |
| 604.0 | 132.3 | 97 | 71 | 73 |

The best immobilization condition is defined as being the result of a compromise between these different yields and the activity of the immobilized biocatalyst obtained.

First of all, it is observed that the use of a solution of free DsrM ΔPS ΔC-APY with higher activity (45 U/ml vs 16 U/ml used during the screening of the supports) makes it possible to significantly increase the activity when fixed on the support. Indeed, the measured activities are increased by a factor of 2 (cf. table 4, activities of the order of 140 U/ml).

Moreover, weights of Purolite ECR8214® support of between 100 and 450 mg make it possible to obtain a fixed activity around 140 U/g. Without wishing to be bound by any theory, the inventors think that under these conditions, the support is totally saturated with protein. This is moreover confirmed by the fixation and immobilization yields obtained which tend to increase with the weight of support used.

Above 600 mg placed in contact with 2.5 ml of sonication supernatant, the activity starts to decrease (approximately 132 U/g).

The best immobilization condition for the Purolite ECR8214® support is therefore placing in contact with an amount of between 450 and 600 mg of support, typically of approximately 500 ml, with 2.5 ml of sonication supernatant. These conditions enable the best activity to be obtained (approximately 140 U/g) while limiting enzyme losses (high yields).

Hereinafter, "immobilized DsrM ΔPS ΔC-APY" is a dextransucrase DsrM ΔPS ΔC-APY immobilized on Purolite ECR8214® support.

Example 7: Determination of the Production Yields of the Whole Dextransucrase DsrM and of the Truncated Dextransucrase DsrM ΔPS ΔC-APY The production yields are determined by anion exchange chromatography (HPAEC-PAD, High Performance Anion Exchange Chromatography with Pulsed Amperometric Detection), and by size exclusion chromatography (HPSEC, High Performance Size Exclusion Chromatography).

HPAEC-PAD Analysis

The sugars, glucose, fructose, leucrose and sucrose are separated on a Dionex CarboPac PA-100 column by means of a sodium acetate gradient of from 6 to 500 mM over 36 min, containing 150 mM of sodium hydroxide. Standard ranges of 5, 10, 15 and 20 mg·kg$^{-1}$ of these sugars are prepared and enable their quantification.

The production yields, that is to say the share of glucose derived from the sucrose, that is incorporated into the formation of free glucose, of leucrose and of dextran, are calculated as follows:

$$\% G \text{ glucose} = \frac{([\text{Glucose}]tf - [\text{Glucose}]t0) \times 342}{([\text{Sucrose}]t0 - [\text{Sucrose}]tf) \times 180} \times 100$$

$$\% G \text{ leucrose} = \frac{([\text{Leucrose}]tf - [\text{Leucrose}]t0)}{([\text{Sucrose}]t0 - [\text{Sucrose}]tf)} \times 100$$

HPSEC Analysis

The sugars are separated as a function of their size on two gel permeation columns placed in series (Shodex OH Pack 805 and 802.5) in an oven, the temperature of which is kept at 70° C. The flow rate of the mobile phase (0.45 M NaNO$_3$, 1% ethylene glycol) is 0.3 ml·min$^{-1}$. The samples are diluted in the same solvent as the eluent at 10 g·l$^{-1}$ maximum total sugars.

Analysis of the reaction products by size exclusion chromatography makes it possible to calculate the share of glucosyl units derived from the sucrose and used in the production of dextran:

$$\%G \text{ dextran} = \frac{Area_{dextran}}{Area_{sucrose} \times \frac{162}{342}}$$

Whole Dextransucrase DsrM

It has been demonstrated here that the enzyme DsrM is a very good polymerase. Indeed, chromatographic analyses (HPAEC-PAD and HPSEC-RI) carried out following dextran synthesis starting from 100 g·l$^{-1}$ of sucrose, at 30° C., pH 5.75, show that 81% of the glucosyl units derived from the substrate are used for the production of dextran. Only 4% and 15% of these units are incorporated into the synthesis of free glucose and of leucrose, respectively.

Truncated Dextransucrase DsrM ΔPS ΔC-APY

It has been demonstrated here that the truncated dextransucrase DsrM ΔPS ΔC-APY is also an excellent polymerase. Indeed, chromatographic analyses (HPAEC-PAD and HPSEC-RI) carried out following dextran synthesis starting from 100 g·l$^{-1}$ of sucrose, at 30° C., pH 5.75, show that 85% of the glucosyl units derived from the substrate are used for the production of the polymer. Only 3% and 12% of these units are lost by incorporation into the synthesis of free glucose and of leucrose, respectively.

Example 8: Method for Determining the Molar Mass of the Dextrans by HPSEC Analysis A standard range produced with commercial dextrans of 503 000, 68 400, 34 100, 11 300 g·mol$^{-1}$, and also maltoheptose, sucrose and fructose, made it possible to determine the molar mass of the dextrans synthesized by DsrM, DsrM ΔPS ΔC-APY or immobilized DsrM ΔPS ΔC-APY.

Example 9: Determination of the Optimal Working Conditions of the Whole Dextransucrase DsrM and of the Truncated Dextransucrase DsrM ΔPS ΔC-APY Effect of Temperature The optimal temperature value is determined by measuring the activity of the crude enzymatic extract at various temperatures (between 23 and 50° C.) starting from 100 g·l$^{-1}$ of sucrose in 50 mM of sodium acetate buffer, pH 5.75.

As can be seen in FIGS. 4 and 5, the truncated dextransucrase DsrM ΔPS ΔC-APY and the dextransucrase DsrM have an optimal temperature of between 30 and 45° C., affording the possibility of working over broad temperature ranges, and especially at high temperatures.

Effect of pH

The effect of pH on the enzymatic activity of the crude extract is measured at 30° C. starting from 100 g·l$^{-1}$ of sucrose, in 50 mM of phosphate citrate buffer, for pH values of between 3.5 and 8 (intervals of 0.5).

As can be seen in FIG. 6, the truncated dextransucrase DsrM ΔPS ΔC-APY has an optimal pH of between 4.5 and 5.5.

As can be seen in FIG. 7, the truncated dextransucrase DsrM has an optimal pH of between 5 and 7.

Example 10: Production of Dextrans of Different Molar Masses

Enzymatic reactions with DsrM, DsrM ΔPS ΔC-APY and immobilized DsrM ΔPS ΔC-APY were carried out at 1 U/mL, starting from different initial sucrose concentrations (50, 100, 200, 300 and 400 g·l$^{-1}$) and optionally at different temperatures (25, 30, 35, 40 and 45° C.), in sodium acetate buffer, 50 mM, pH 5.75.

Samples were taken at starting and finishing times (24 h) (the enzymatic reaction was stopped by heating at 95° C. for 5 minutes) and stored at −20° C. before being analyzed by HPAEC-PAD, as explained in example 7, in order to control the production yields, and by size exclusion chromatography (HPSEC), as explained in example 8, in order to determine the molecular weight of the dextrans synthesized.

As regards the assays on immobilized DsrM ΔPS ΔC-APY, the reaction media are centrifuged in order to eliminate the solid residues of the immobilized enzyme.

Whole Dextransucrase DsrM

A linear variation in the size of the products as a function of the initial sucrose concentration is observed (temperature fixation).

It is thus possible to control the molar mass of the dextran synthesized by the whole form of DsrM, by varying the initial substrate concentration, at fixed temperature.

Thus, for example at 25° C., it is possible to obtain a panel of dextrans, the average molar mass of which varies between 32×10$^3$ and 6.5×10$^3$ g·mol$^{-1}$ over a range of initial substrate concentrations extending from 100 to 500 g·l$^{-1}$ (FIG. 8).

FIG. 9 demonstrates that a dextran synthesized starting from 100 g·l$^{-1}$ of sucrose alone, at 30° C. and pH 5.75, has a low average molar mass of 27·10$^3$ Da, and is barely poly disperse.

Truncated Dextransucrase DsrM ΔPS ΔC-APY

As can be seen in FIGS. 10 and 11, a linear variation in the size of the products as a function of the temperature (fixation of the initial sucrose concentration) or of the initial sucrose concentration (temperature fixation) is observed.

It is thus possible to very precisely control the molar mass of the dextran synthesized by the truncated dextransucrase DsrM ΔPS ΔC-APY, by varying the initial substrate concentration, at fixed temperature (or vice-versa).

Thus, by way of example, by fixing the temperature at 25° C., the truncated dextransucrase DsrM ΔPS ΔC-APY produces a dextran of an average molar mass of 25×10$^3$ g·mol$^{-1}$ starting from 50 g·l$^{-1}$ of sucrose and a dextran of an average molar mass of 8×10$^3$ g·mol$^{-1}$ starting from 400 g·l$^{-1}$ of sucrose.

Moreover, it is noted that the dextrans synthesized are barely polydisperse, with the exception of the polymers produced starting from high sucrose concentration (400 g·l$^{-1}$).

It is also noted that it is possible to cover a broader spectrum of products, in terms of molecular weights, at low temperatures or starting from low sucrose concentrations.

Similarly, at an initial sucrose concentration fixed at 50 g·l$^{-1}$, it is possible to obtain dextrans, the average molar mass of which is between 25×10$^3$ g·mol$^{-1}$ and 7×10$^3$ g·mol$^{-1}$ over a temperature range extending from 25 to 45° C.

Moreover, the production outcomes hardly vary as a function of the experimental conditions. The HPAEC-PAD analyses carried out show that for all the reactions tested, more than 81% of the glucosyl units derived from the substrate are used for the production of the polymer during the use of the truncated dextransucrase DsrM ΔPS ΔC-APY.

FIG. 12 demonstrates that a dextran synthesized starting from 100 g·l$^{-1}$ of sucrose alone, at 30° C. and pH 5.75, has a low average molar mass of 17.5$^3$ Da, and is barely poly disperse.

Immobilized Dextransucrase DsrM ΔPS ΔC-APY

As can be seen in FIG. 13, the immobilized enzyme retains its ability to produce dextrans of different molar masses depending on the initial sucrose concentration. The linear variation in the molar mass of the dextrans produced is also retained.

Moreover, the dispersity of the dextrans obtained is similar between the two enzyme forms (dextransucrase DsrM ΔPS ΔC-APY and immobilized dextransucrase DsrM ΔPS ΔC-APY) (FIG. 13).

Finally, the dextransucrase DsrM ΔPS ΔC-APY immobilized on Purolite ECR8214® support has the particularity of producing dextrans of lower molar masses than those produced by the dextransucrase DsrM ΔPS ΔC-APY under identical conditions. For example, for an initial concentration of 100 g·l$^{-1}$ of sucrose, a dextran of a molar mass of 9.4×10$^3$ g·mol$^{-1}$ is obtained with the non-immobilized dextransucrase DsrM ΔPS ΔC-APY whereas a dextran of a molar mass of 4.7×10$^3$ g·mol$^{-1}$ is obtained with the immobilized dextransucrase DsrM ΔPS ΔC-APY (FIG. 13). The immobilization of a dextransucrase according to the invention therefore has the advantage of broadening the range of dextrans produced.

Example 11: Analysis of the Nature of the Bonds of the Dextrans Produced by the Whole Dextransucrase DsrM and by the Truncated Dextransucrase DsrM ΔPS ΔC-APY After lyophilization, 20 mg of crude reaction medium (after total consumption of the sucrose) are diluted in 0.5 ml of deuterated water and analyzed by proton NMR with the Bruker Avance spectrometer (500 MHz). The spectra are then processed and interpreted using the TOPSPIN 3.0 software.

Whole Dextransucrase DsrM

It was demonstrated by the NMR analyses that the product synthesized from DsrM and 100 g·l$^{-1}$ of sucrose alone, at 30° C. in 50 mM of sodium acetate, pH 5.75, is a polymer of glucosyl units bonded exclusively (100%) in α-1,6 (FIG. 14).

The product synthesized from DsrM is therefore a perfectly linear dextran, and DsrM is a dextransucrase which is very specific to polymerization by α-1,6-type glycosidic bonds.

Truncated Dextransucrase DsrM ΔPS ΔC-APY

It was demonstrated by the NMR analyses that, just as for the dextransucrase DsrM, the product synthesized from the truncated form DsrM ΔPS ΔC-APY and 100 g·l$^{-1}$ of sucrose alone, at 30° C. and pH 5.75, is a polymer of glucosyl units bonded exclusively (100%) in α-1,6 (FIG. 15).

The product synthesized from the truncated form DsrM ΔPS ΔC-APY is therefore a perfectly linear dextran, and DsrM ΔPS ΔC-APY is a dextransucrase which is very specific to polymerization by α-1,6-type glycosidic bonds.

Example 12: Production of Glucooligosaccharides by Acceptor Reaction

Acceptor reactions were carried out using 1 U·ml$^{-1}$ of DsrM ΔPS ΔC-APY and immobilized DsrM ΔPS ΔC-APY, starting from initial sucrose concentrations varying from 60 to 333 g·l$^{-1}$ and from glucose concentrations (in the role of carbohydrate acceptor) varying from 83 to 333 g·l$^{-1}$. The syntheses took place at a temperature of 30° C. and in sodium acetate buffer, 50 mM, pH 5.75. The enzymatic reactions were stopped by heating at 95° C. for 5 minutes after 24 hours.

The different samples were then analyzed by HPSEC as explained in example 8 in order to determine the average molar mass of the products synthesized.

The results obtained for DsrM ΔPS ΔC-APY, i.e. the protein with dextransucrase activity having the sequence SEQ ID NO: 2 as amino acid sequence, starting from different sucrose concentrations and glucose acceptor concentrations, are presented in table 5 below:

TABLE 5

| [Glucose]/ [Sucrose] ratio$^a$ | Total dry weight (g·l$^{-1}$) | Glucose (g·l$^{-1}$) | Sucrose (g·l$^{-1}$) | Glucooligosaccharides molar mass (g·mol$^{-1}$) |
|---|---|---|---|---|
| 1.25 | 375 | 167 | 208 | 1.9 × 10$^3$ |
| 2.31 | 375 | 113 | 262 | 2.7 × 10$^3$ |
| 1.25 | 198 | 88 | 110 | 3.4 × 10$^3$ |
| 0.50 | 500 | 333 | 167 | 0.8 × 10$^3$ |
| 1.25 | 375 | 167 | 208 | 1.9 × 10$^3$ |
| 0.19 | 375 | 315 | 60 | 0.7 × 10$^3$ |
| 1.25 | 552 | 245 | 307 | 1.1 × 10$^3$ |
| 2.00 | 500 | 167 | 333 | 1.6 × 10$^3$ |
| 1.25 | 375 | 167 | 208 | 1.9 × 10$^3$ |
| 0.50 | 250 | 167 | 83 | 1.6 × 10$^3$ |
| 2.00 | 250 | 83 | 167 | 1.6 × 10$^3$ |
| 1.25 | 375 | 167 | 208 | 1.9 × 10$^3$ |

$^a$Ratio calculated from concentrations by weight

The results obtained for immobilized DsrM ΔPS ΔC-APY, i.e. the protein with dextransucrase activity having the sequence SEQ ID NO: 2 as amino acid sequence, immobilized on ECR8214® as described in example 6, starting from different sucrose concentrations and glucose acceptor concentrations, are presented in table 6 below:

TABLE 6

| [Glc]/ [Sucrose] ratio$^a$ | Total dry weight (g·l$^{-1}$) | [Glucose] (g·l$^{-1}$) | [Sucrose] (g·l$^{-1}$) | Glucooligosaccharides molar mass (g·mol$^{-1}$) |
|---|---|---|---|---|
| 1.25 | 375 | 167 | 208 | 1.5 × 10$^3$ |
| 2.31 | 375 | 113 | 262 | 2.0 × 10$^3$ |
| 1.25 | 198 | 88 | 110 | 2.4 × 10$^3$ |
| 0.50 | 500 | 333 | 167 | 0.7 × 10$^3$ |
| 1.25 | 375 | 167 | 208 | 1.6 × 10$^3$ |
| 0.19 | 375 | 315 | 60 | 0.7 × 10$^3$ |
| 1.25 | 552 | 245 | 307 | 1.0 × 10$^3$ |
| 2.00 | 500 | 167 | 333 | 1.4 × 10$^3$ |
| 1.25 | 375 | 167 | 208 | 1.6 × 10$^3$ |
| 1.25 | 375 | 167 | 208 | 1.5 × 10$^3$ |
| 0.50 | 250 | 167 | 83 | 1.5 × 10$^3$ |
| 2.00 | 250 | 83 | 167 | 2.3 × 10$^3$ |
| 1.25 | 375 | 167 | 208 | 1.6 × 10$^3$ |

$^a$Ratio calculated from concentrations by weight

Thus, it has been demonstrated here that, with the synthesis conditions used, the use of dextransucrases according to the invention makes it possible at least to synthesize glucooligosaccharides of a medium molar mass ranging from 0.7×10$^3$ to 3.4×10$^3$ g·mol$^{-1}$.

Example 13

The commercial dextran of 11 300 g/mol supplied by Sigma (ref D-9260, batch 74H0764) was compared to the dextran synthesized by the process of the invention starting from 300 g/l of sucrose in sodium acetate buffer at pH 5.75 and a temperature of 30° C. in order to obtain a molar mass of 11 300 g/mol. Analysis by size exclusion chromatography on Shodex SB-805 and SB-802.5 columns in series shows that the population of dextrans obtained by virtue of the process of the invention is markedly less polydisperse than the commercial dextran.

REFERENCES (1) Mage and Kabat, Immunochemical studies on dextrans; III. The specificities of rabbit antidextrans. Further findings on antidextrans with 1,2- and 1,6-specificities; 1963; Vol. 91, p. 634-640
(2) De Belder, Dextran; Amersham Biosciences; 2003
(3) Glucansucrases: Three-dimensional structures, reactions, mechanism, alpha-glucan analysis and their implications in biotechnology and food applications Lemhuis et al., Journal of Biotechnology, January 2013, vol 163, Issue 2, 250-272
(4) A method for determination of invertase activity, Sumner & Howell, Journal of biological chemistry, 1935, vol 108, Issue 51

(5) Moulis C, Vaca Medina G, Suwannarangsee S, Monsan P, Remaud-Simeon M, Potocki-Veronese G (2008) One-step synthesis of isomalto-oligosaccharide syrups and dextrans of controlled size using engineered dextransucrase. Biocatal. Biotransformation. Taylor & Francis, pp 141-151

(6) Kim et al., Dextran molecular size and degree of branching as a function of sucrose concentration, pH, and temperature of reaction of *Leuconostoc mesenteroides* B-512FMCM dextransucrase; Carbohydrate Research 338 (2003) 1183-1189

(7) High-level production and purification of a fully active recombinant dextransucrase from *Leuconostoc mesenteroides* NRRL B-512F, Moulis et al, FEMS Microbiology Letters, August 2006, vol 261, Issue 2, 203-210

(8) Kothari et al, Structural Characterization of Enzymatically Synthesized Dextran and Oligosaccharides from *Leuconostoc mesenteroides* NRRL B-1426 Dextransucrase. ISSN 0006-2979, Biochemistry (Moscow), 2013, Vol. 78, No. 10, pp. 1164-1170.

(9) Amari et al, Characterization of a novel dextransucrase from *Weissella confusa* isolated from sourdough. Appl Microbiol Biotechnol (2013) 97:5413-5422

(10) Kralj et al, Glucan synthesis in the genus *Lactobacillus*: isolation and characterization of glucansucrase genes, enzymes and glucan products from six different strains; Microbiology (2004), 150, 3681-3690.

(11) Striegel et al, An SEC/MALS study of alternan degradation during size-exclusion chromatographic analysis; Anal Bioanal Chem (2009) 394:1887-1893

(12) Dextran: effect of process parameters on production, purification and molecular weight and recent applications, Vettori et al., Dialogos & Ciencia, ISSN 1678-0493, no 31, September 2012

(13) GOULAS, A. K. et al. Synthesis of isomaltoligosaccharides and oligodextrans by the combined use of dextransucrase and dextransase. Enzyme Microb. Technol., 35, 2004. 327-338.

(14) Naessens et al., M. et al. *Leuconostoc* dextransucrase and dextran: production, properties and applications. J. Chem. Technol. Biotechnol., 80, 2005. 845-860.

(15) EGGLESTON AND COTE, G. L. Oligosaccharides in food and agriculture. Washington, D.C.: ACS symposium series 849, 2003. p. 1-15.

(16) Functional Polymers Based on Dextran, Thomas Heinze, Tim Liebert, Brigitte Heublein, Stephanie Hornig, Adv Polym Sci (2006) 205: 199-291, DOI 10.1007/12_100.

(17) Structure and macromolecular properties of *Weissella confusa* and *Leuconostoc citreum* dextrans with a potential application in sourdough, Ndegwa Henry Maina, 1 Jun. 2012, University of Helsinki, Department of Food and Environmental Sciences, Chemistry and Biochemistry Division.

The invention claimed is:

1. A process for synthesizing dextrans comprising:
forming dextrans by contacting sucrose in a synthesis medium with
(a) a protein with dextransucrase activity where the protein is at least 95% identical to SEQ ID NO: 1 or
(b) a protein with dextransucrase activity where the protein is at least 98% identical to SEQ ID NO: 1.

2. A process for synthesizing dextrans comprising:
forming dextrans by contacting sucrose in a synthesis medium with
(a) a complex comprising a support and a protein with dextransucrase activity where the protein is at least 95% identical to SEQ ID NO: 1 or
(b) a complex comprising a support and a protein with dextransucrase activity where the protein is at least 98% identical to SEQ ID NO: 1.

3. The process of claim 1, wherein the step of contacting to form dextrans is carried out either at a temperature of between 20° C. and 50° C., or at a temperature of between 25° C. and 45° C.

4. The process of claim 1, wherein the sucrose is present in the synthesis medium at either a concentration of between 50 and 600 g·l$^{-1}$, or a concentration of between 50 and 400 g·l$^{-1}$.

5. The process of claim 1, wherein the step of contacting to form dextrans takes place either at a pH that is between 4 and 7, or at a pH of approximately 5.75.

6. A process for synthesizing glucooligosaccharides comprising:
forming glucooligosaccharides by contacting a synthesis medium that comprises sucrose and at least one carbohydrate acceptor with
(a) a protein with dextransucrase activity where the protein is at least 95% identical to SEQ ID NO: 1 or
(b) a protein with dextransucrase activity where the protein is at least 98% identical to SEQ ID NO: 1.

7. A process for synthesizing glucoconjugate compound comprising:
forming glucoconjugate compounds by contacting synthesis medium that comprises sucrose and at least one hydroxylated molecule with
(a) a protein with dextransucrase activity where the protein is at least 95% identical to SEQ ID NO: 1 or
(b) a protein with dextransucrase activity where the protein is at least 98% identical to SEQ ID NO: 1 and position 563 to 1282 within SEQ ID NO: 1.

8. A process for synthesizing glucooligosaccharides comprising:
(i) forming glucooligosaccharides by contacting a synthesis medium that comprises sucrose and at least one carbohydrate acceptor with
(a) a complex comprising a support and a protein with dextransucrase activity where the protein is at least 95% identical to SEQ ID NO: 1 or
(b) a complex comprising a support and a protein with dextransucrase activity where the protein is at least 98% identical to SEQ ID NO: 1.

9. A process for synthesizing glucoconjugate compounds comprising:
forming a glucoconjugate compounds by contacting a synthesis medium that comprises sucrose and at least one hydroxylated molecule with
(a) a complex comprising a support and a protein with dextransucrase activity where the protein is at least 95% identical to SEQ ID NO: 1 or
(b) a complex comprising a support and a protein with dextransucrase activity where the protein is at least 98% identical to SEQ ID NO: 1,
wherein said protein with dextransucrase activity has been immobilized on said support.

10. The process of claim 1, wherein the protein with dextransucrase activity is selected from
(a) a protein with dextransucrase activity where the protein is at least 95% identical to SEQ ID NO: 2 or
(b) a protein with dextransucrase activity where the protein is at least 98% identical to SEQ ID NO: 2.

11. The process of claim 10, wherein the protein with dextransucrase activity comprises the amino acid sequence set forth in SEQ ID NO: 2.

12. The process of claim 2, wherein the protein with dextransucrase activity is selected from
(a) a protein with dextransucrase activity where the protein is at least 95% identical to SEQ ID NO: 2 or
(b) a protein with dextransucrase activity where the protein is at least 98% identical to SEQ ID NO: 2.

13. The process of claim 12, wherein the protein with dextransucrase activity comprises the amino acid sequence set forth in SEQ ID NO: 2.

14. The process of claim 6, wherein the protein with dextransucrase activity is selected from
(a) a protein with dextransucrase activity where the protein is at least 95% identical to SEQ ID NO: 2 or
(b) a protein with dextransucrase activity where the protein is at least 98% identical to SEQ ID NO: 2.

15. The process of claim 14, wherein the protein with dextransucrase activity comprises the amino acid sequence set forth in SEQ ID NO: 2.

16. The process of claim 7, wherein the protein with dextransucrase activity is selected from
(a) a protein with dextransucrase activity where the protein is at least 95% identical to SEQ ID NO: 2 or
(b) a protein with dextransucrase activity where the protein is at least 98% identical to SEQ ID NO: 2.

17. The process of claim 16, wherein the protein with dextransucrase activity comprises the amino acid sequence set forth in SEQ ID NO: 2.

18. The process of claim 8 wherein the protein with dextransucrase activity is selected from
(a) a protein with dextransucrase activity where the protein is at least 95% identical to SEQ ID NO: 2 or
(b) a protein with dextransucrase activity where the protein is at least 98% identical to SEQ ID NO: 2.

19. The process of claim 18, wherein the protein with dextransucrase activity comprises the amino acid sequence set forth in SEQ ID NO: 2.

20. The process of claim 9, wherein the protein with dextransucrase activity is selected from
(a) a protein with dextransucrase activity where the protein is at least 95% identical to SEQ ID NO: 2 or
(b) a protein with dextransucrase activity where the protein is at least 98% identical to SEQ ID NO: 2.

21. The process of claim 20, wherein the protein with dextransucrase activity comprises the amino acid sequence set forth in SEQ ID NO: 2.

* * * * *